US011494724B2

(12) United States Patent
Cline et al.

(10) Patent No.: US 11,494,724 B2
(45) Date of Patent: Nov. 8, 2022

(54) OUTCOMES AND PERFORMANCE MONITORING

(71) Applicant: Lightbeam Health Solutions, LLC, Irving, TX (US)

(72) Inventors: Patrick Cline, Irving, TX (US); Jerry Shultz, Irving, TX (US); James Michael Hoxter, Jr., Irving, TX (US); Robert Nary, Irving, TX (US)

(73) Assignee: Lightbeam Health Solutions, LLC, Iriving, TX (US)

( * ) Notice: Subject to any disclaimer, the term of this patent is extended or adjusted under 35 U.S.C. 154(b) by 533 days.

(21) Appl. No.: 15/212,055

(22) Filed: Jul. 15, 2016

(65) Prior Publication Data

US 2016/0358116 A1    Dec. 8, 2016

Related U.S. Application Data

(63) Continuation-in-part of application No. 14/449,098, filed on Jul. 31, 2014.

(60) Provisional application No. 62/192,832, filed on Jul. 15, 2015, provisional application No. 61/860,509, filed on Jul. 31, 2013.

(51) Int. Cl.
  *G06Q 10/06*    (2012.01)
  *G16H 50/30*    (2018.01)
  *G16H 10/60*    (2018.01)

(52) U.S. Cl.
  CPC . *G06Q 10/06398* (2013.01); *G06Q 10/06393* (2013.01); *G06Q 10/063114* (2013.01); *G16H 10/60* (2018.01); *G16H 50/30* (2018.01)

(58) Field of Classification Search
  None
  See application file for complete search history.

(56) References Cited

U.S. PATENT DOCUMENTS

| 8,515,777 B1 * | 8/2013 | Rajasenan | G06Q 10/06313 705/2 |
| 2002/0029161 A1 * | 3/2002 | Brodersen | G06Q 10/1093 705/7.14 |

(Continued)

OTHER PUBLICATIONS

Dale Shallerand David Kanouse, Private "Performance Feedback" Reporting for Physicians, Nov. 2012, Agency for Healthcare Research and Quality, publication No. 13-0004 (Year: 2012).*

(Continued)

*Primary Examiner* — Christopher L Gilligan
*Assistant Examiner* — Karen A Hranek
(74) *Attorney, Agent, or Firm* — Reising Ethington P.C.

(57) ABSTRACT

A system for selecting a health care provider and then monitoring and reporting the selected provider's performance. A processor is programmed to retrieve from the internet and store in a database historical performance data on providers and healthcare data relating to the providers' historical performance. The processor determines which provider should be selected to perform a task, by assessing the providers' historical performances against each other; selecting a provider to perform a task, monitoring post-selection healthcare data relating to the provider's performance of the task, and generating a reporting metric comprising a display of a trend in the selected provider's historical performance and/or the provider's current performance of the task.

10 Claims, 26 Drawing Sheets

(56) References Cited

U.S. PATENT DOCUMENTS

| | | | | |
|---|---|---|---|---|
| 2006/0053035 | A1* | 3/2006 | Eisenberg | G06Q 50/22 705/2 |
| 2006/0241974 | A1* | 10/2006 | Chao | G06Q 10/00 705/2 |
| 2006/0282302 | A1* | 12/2006 | Hussain | G16H 40/20 705/2 |
| 2006/0287906 | A1* | 12/2006 | McGillin | G16H 40/20 705/2 |
| 2007/0142713 | A1* | 6/2007 | Lancaster | G06Q 50/22 600/300 |
| 2008/0040206 | A1* | 2/2008 | Silvera | G06Q 10/00 705/7.42 |
| 2008/0059292 | A1* | 3/2008 | Myers | G06Q 10/06 705/7.39 |
| 2008/0228549 | A1* | 9/2008 | Harrison | G06Q 10/06 705/7.14 |
| 2009/0043634 | A1* | 2/2009 | Tisdale | G06Q 10/06 705/2 |
| 2009/0063238 | A1* | 3/2009 | Storzum | G06Q 10/06398 705/7.42 |
| 2009/0307010 | A1* | 12/2009 | Boehmer-Lasthaus | G06Q 10/06 705/2 |
| 2010/0169119 | A1* | 7/2010 | Hussain | G06Q 10/06 705/3 |
| 2011/0077973 | A1* | 3/2011 | Breitenstein | G06F 3/0484 705/3 |
| 2011/0191115 | A1* | 8/2011 | Zalam | G06Q 10/10 705/2 |
| 2011/0246224 | A1* | 10/2011 | Green, III | G06Q 10/06 705/2 |
| 2012/0116985 | A1* | 5/2012 | Rastogi | G06Q 30/018 705/317 |
| 2012/0143013 | A1 | 6/2012 | Davis, III et al. | |
| 2013/0018686 | A1* | 1/2013 | Wright | G06Q 10/06311 705/7.14 |
| 2013/0151298 | A1* | 6/2013 | Davis | G06Q 10/06311 705/7.14 |
| 2013/0173355 | A1* | 7/2013 | Barcenas | G06Q 10/06393 705/7.39 |
| 2013/0262132 | A1* | 10/2013 | Sant | G06Q 10/06398 705/2 |
| 2013/0262357 | A1* | 10/2013 | Amarasingham | G16H 50/70 706/21 |

OTHER PUBLICATIONS

Healthcare Effectiveness Data and Information Set, Wikipedia, Nov. 13, 2012 (Year: 2012).*

Overview of TCP/IP, Aug. 23, 2002, Sams (Year: 2002).*

* cited by examiner

Measures for Use in Establishing Quality Performance Standards that ACOs Must Meet for Shared Savings

| ACO # | Domain | Measure Title | NQF Measure #/ Measure Steward | Method of Data Submission | P4P Phase-in PY1 | P4P Phase-in PY2 | P4P Phase-in PY3 |
|---|---|---|---|---|---|---|---|
| 12. | Care Coordination/ Patient Safety | Medication Reconciliation | NQF #97 AMA-PCPI/NCQA | GPRO Web Interface | R | P | P |
| 13. | Care Coordination/ Patient Safety | Falls: Screening for Future Fall Risk | NQF #101 NCQA | GPRO Web Interface | R | P | P |
| AIM: Better Health for Populations | | | | | | | |
| 14. | Preventive Health | Influenza Immunization | NQF #41 AMA-PCPI | GPRO Web Interface | R | P | P |
| 15. | Preventive Health | Pneumococcal Vaccination for Patients 65 Years and Older | NQF #43 NCQA | GPRO Web Interface | R | P | P |
| 16. | Preventive Health | Body Mass Index (BMI) Screening and Follow-Up | NQF #421 CMS | GPRO Web Interface | R | P | P |
| 17. | Preventive Health | Tobacco Use: Screening and Cessation Intervention | NQF #28 AMA-PCPI | GPRO Web Interface | R | P | P |
| 18. | Preventive Health | Screening for Clinical Depression and Follow-Up Plan | NQF #418 CMS | GPRO Web Interface | R | P | P |
| 19. | Preventive Health | Colorectal Cancer Screening | NQF #34 NCQA | GPRO Web Interface | R | R | P |
| 20. | Preventive Health | Breast Cancer Screening | NQF #31 NCQA | GPRO Web Interface | R | R | P |
| 21. | Preventive Health | Screening for High Blood Pressure and Follow-Up Documented | CMS | GPRO Web Interface | R | R | P |
| 22. | At Risk Population—Diabetes | Diabetes Composite (All or Nothing Scoring): Diabetes Mellitus: Hemoglobin A1c Control (<8 percent) | NQF #729 MN Community Measurement | GPRO Web Interface | R | P | P |
| 23. | At Risk Population—Diabetes | Diabetes Composite (All or Nothing Scoring): Diabetes Mellitus: Low Density Lipoprotein Control | NQF #729 MN Community Measurement | GPRO Web Interface | R | P | P |

| Task ID # | Task Weight Index Task Name | Task Weight |
|---|---|---|
| 1 | ACO Measure 22 Gap | 5 |
| 2 | Hospital Admit - High Cost patient | 7 |
| 3 | Hospital Discharge - High Cost patient | 8 |
| 4 | Notified of Drug - Drug interaction | 10 |
| 5 | ACO Measure - Flu Shot | 2 |
| ... | | |

Figure 7

Supervisor Home

OUTCOMES AND PERFORMANCE MONITORING

CROSS-REFERENCES TO RELATED APPLICATIONS

This application is a continuation-in-part of U.S. patent application Ser. No. 14/449,098, filed Jul. 31, 2014, which claims the benefit of U.S. Provisional Application Ser. No. 61/860,509, filed Jul. 31, 2013, and both of which are incorporated herein in their respective entireties. This application also claims priority in U.S. Provisional Patent Application Ser. No. 62/192,832 file Jul. 15, 2015, which is also incorporated herein in its entirety, by reference.

STATEMENT REGARDING FEDERALLY SPONSORED RESEARCH OR DEVELOPMENT

Not Applicable

BACKGROUND

Field

This application relates generally to health care service provider selection and performance and outcome monitoring.

Description of Related Art Including Information Disclosed Under 37 CFR 1.97 and 1.98

In response to ever-increasing healthcare costs and poor quality healthcare service delivery, the largest purchaser, the Federal Government, has begun tying income to payer and provider quality measures and outcomes. The government and a number of quality improvement organizations have created performance measurements and effective methods for measuring value, compliance with care guidelines, and quality measures. Yet, the very same payer and provider organizations whose income will increasingly be tied to their performance against these measures, lack an effective and automated solution that measures, tracks, and graphically presents performance. What payers, providers and care managers need, is a way to quantify, measure and compare quality scores, quality score trends, workload, tasks assigned, tasks completed or the overall efficiency and productivity of each provider, care managers and providers care teams. They also need a way to effectively measure and trend performance against quality scores over time.

SUMMARY

A system is provided for selecting a health care provider from a group of health care providers, and then monitoring and reporting the selected provider's performance. The system may include a database and a processor connected to the database and to the internet. The processor may be programmed to retrieve from the internet and store in the database historical performance data on each provider in the group and healthcare data relating to the health care providers' historical performance. The processor may also be programmed to determine whether the provider should be selected to perform a task, by assessing the providers' historical performances against each other; selecting from the group of providers a provider to perform a task, monitoring post-selection healthcare data relating to the provider's performance of the task, and generating a reporting metric comprising a display of a trend in the selected provider's historical or current performance of the task.

DRAWING DESCRIPTIONS

Advantages of the disclosure will be readily appreciated as the same becomes better understood by reference to the following detailed description when considered in connection with the accompanying drawings, wherein:

FIG. 1 is a workflow diagram with an illustrative embodiment of a health care service provider selection and performance and outcome monitoring system including data integration services, data from an EHR combined with information from other sources in an EDW and then being compared to guidelines in a rule builder, a rule warehouse, a rules engine, care management, analytics and utilization management systems, and external rules sources and external care management systems;

FIG. 6 shows a sampling of health quality measures that are stored in rules library (LB Rules Library 150) of the system and are used to measure and compare provider and care manager performance;

FIG. 7 shows a sampling from a task weighting index of the system that are stored in a rules library (LB Rules Library 150) and used by the system to calculate provider and care manager efficiency and workload;

Figure 8:
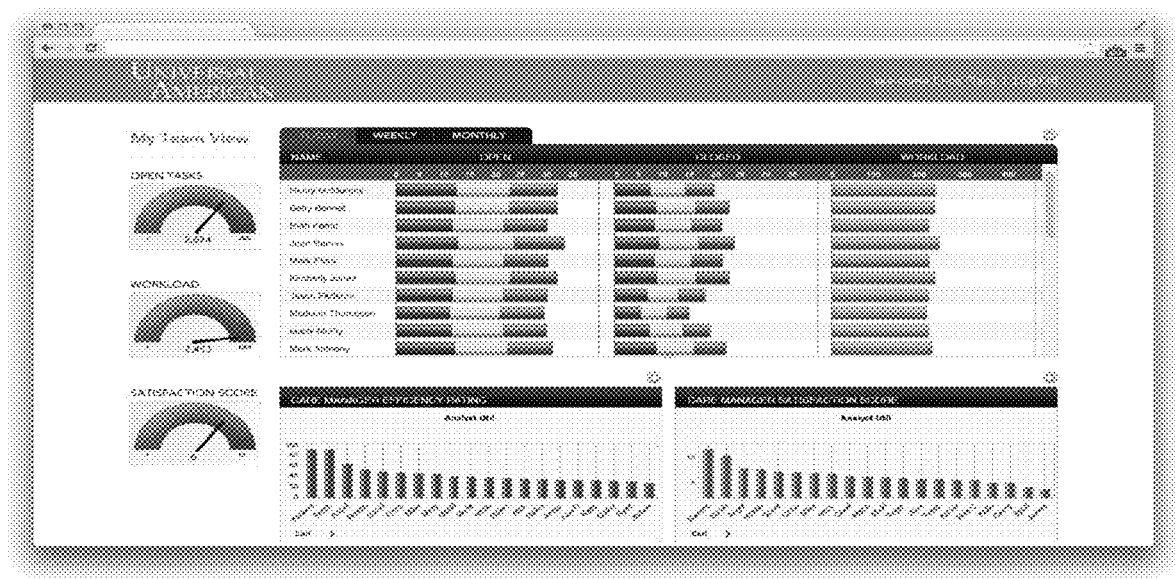
FIG. 8 shows a system screen called "Supervisor View", which represents one way the system allows this data to be consumed and presented in a graphical manner, and also illustrates how the system tracks and presents open tasks, closed tasks, and total weighted tasks that are assigned to a provider or care manager.
Figure 9:
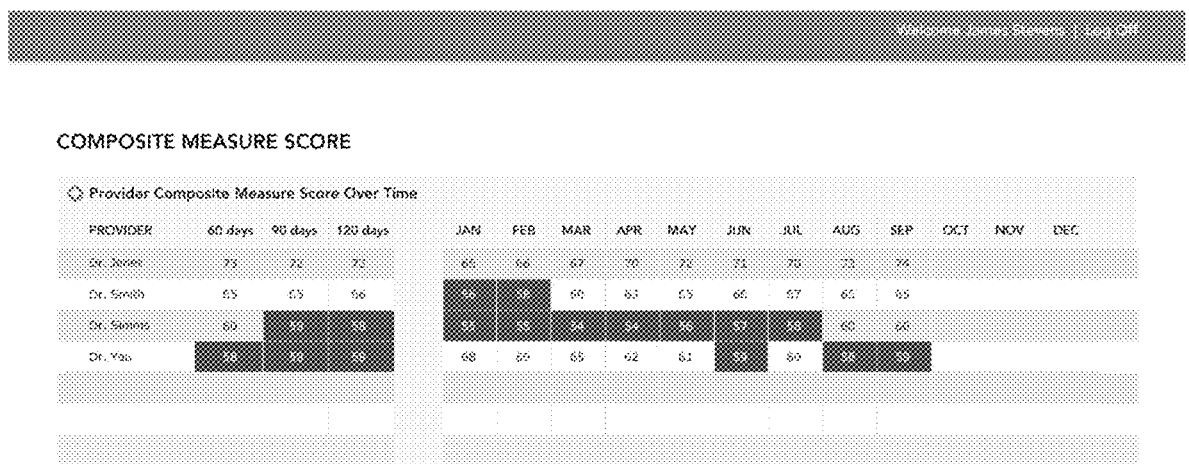
FIG. 9 shows a system screen that depicts one of many ways that quality scores can be represented graphically, color coded and trended over time, with historical provider performance data being sorted in EDW 140.
Figure 10:
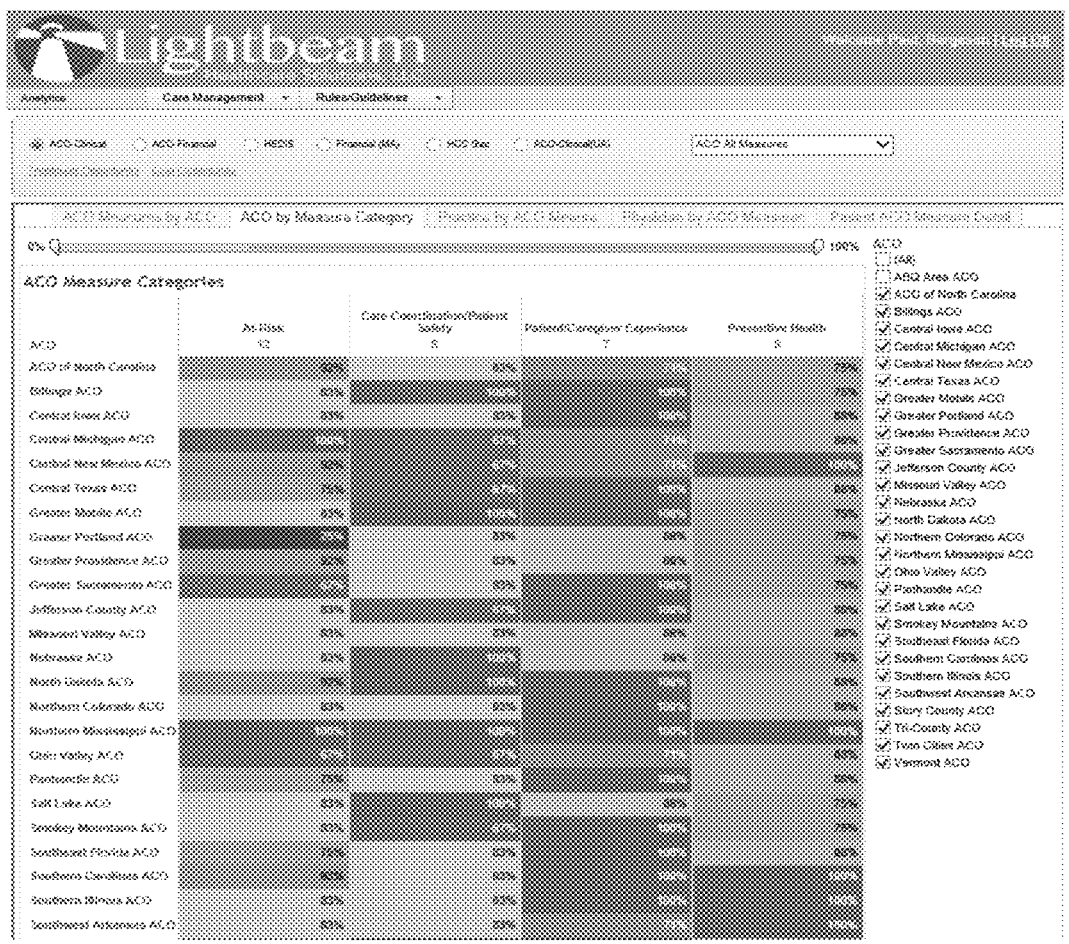
Figure 11:
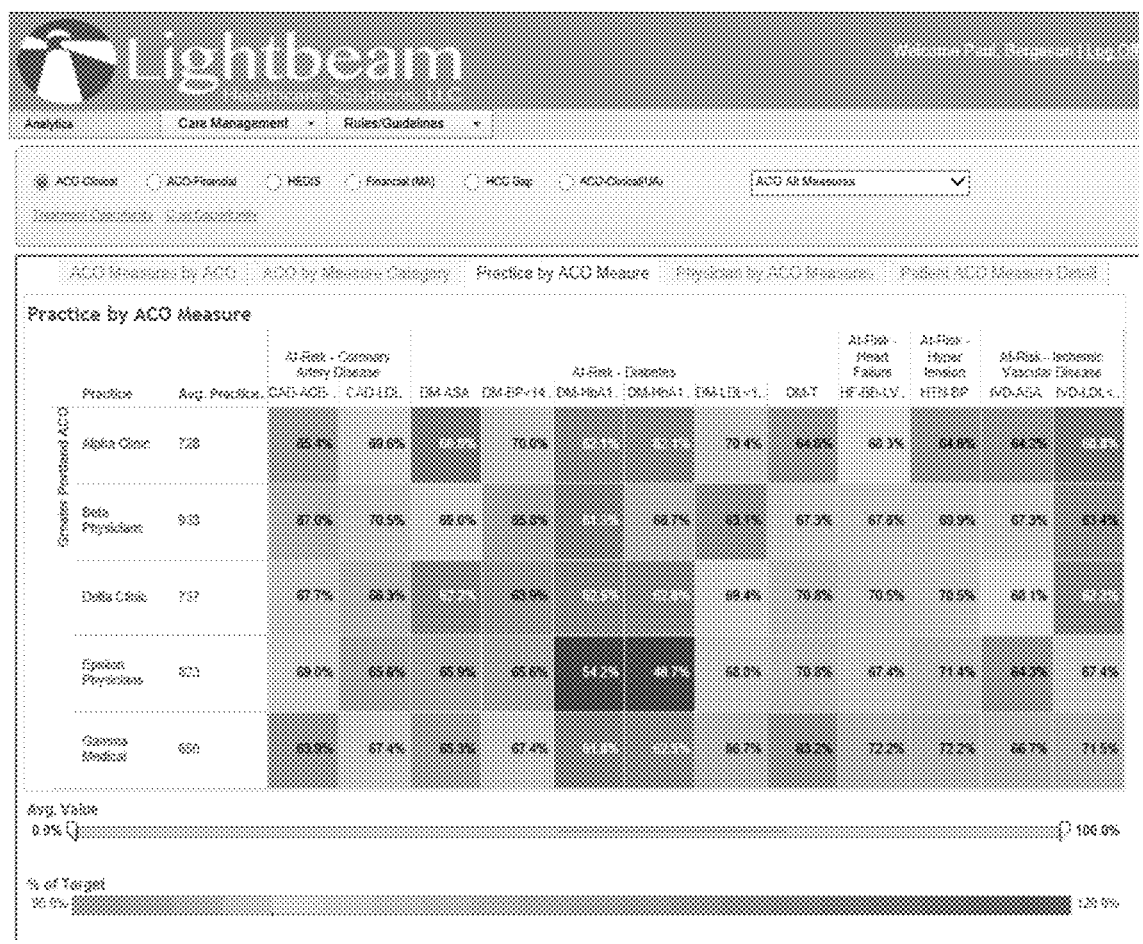
Figure 12:
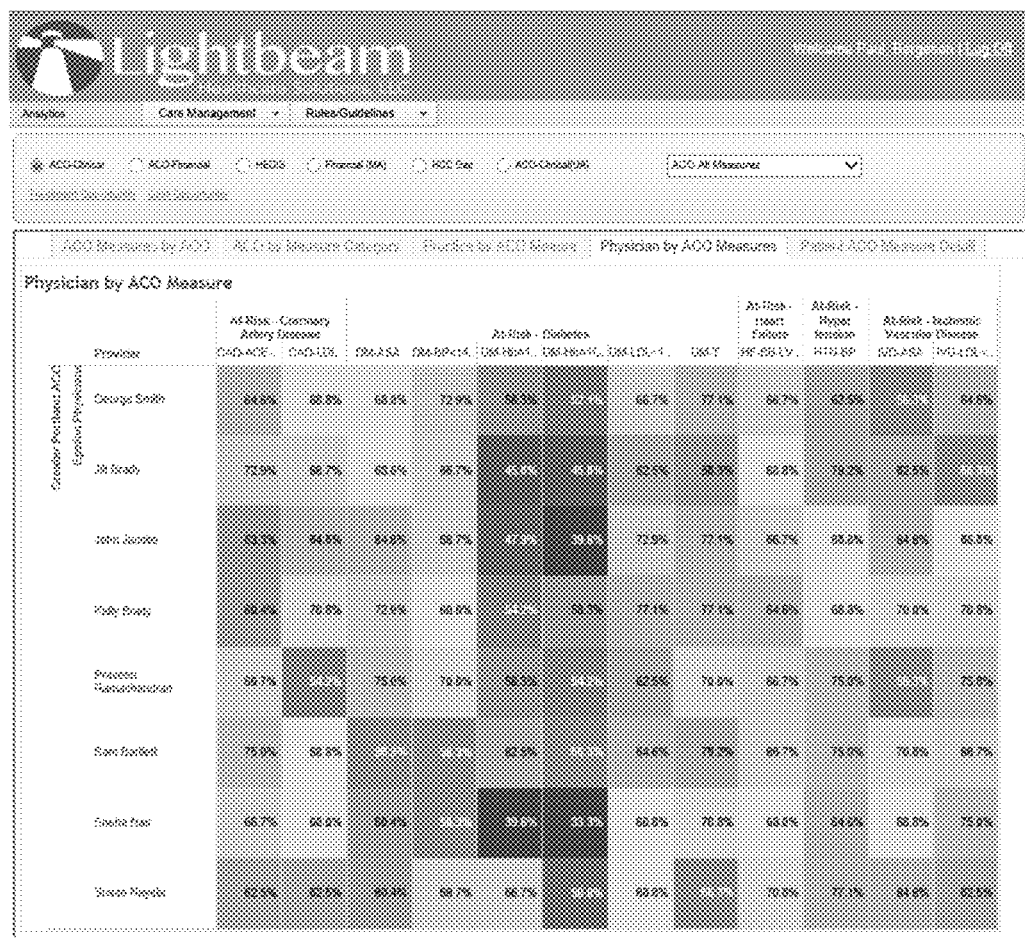
Figure 13:
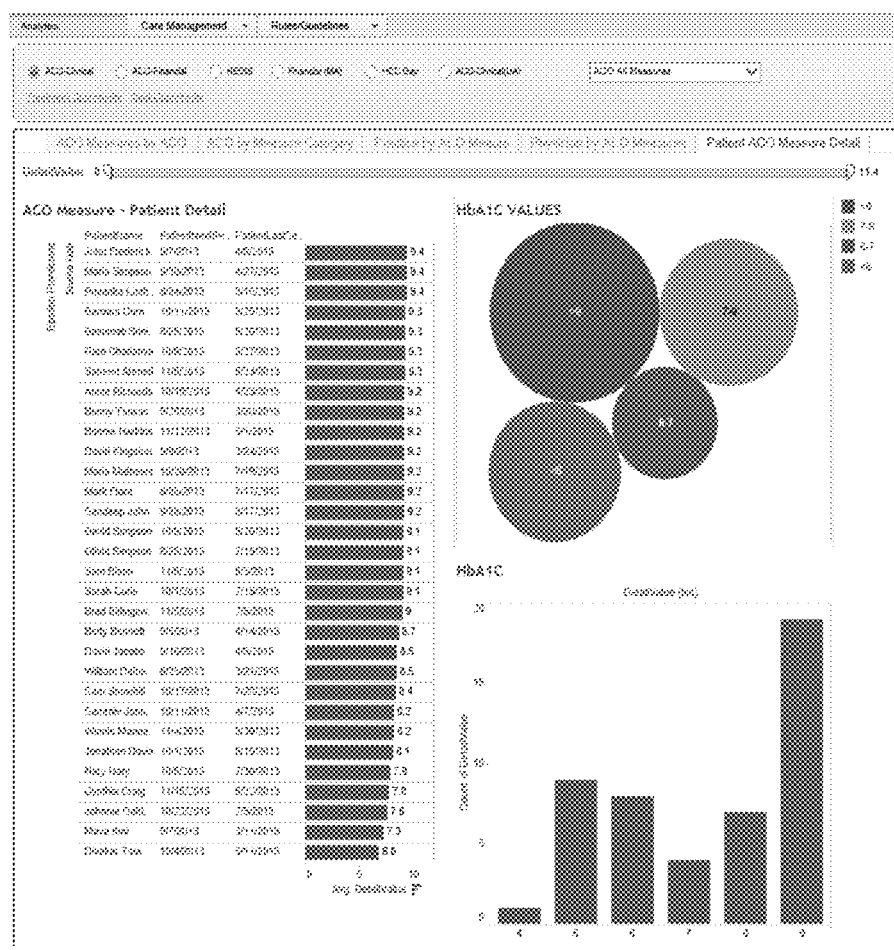
Figure 14:
Figure 15:
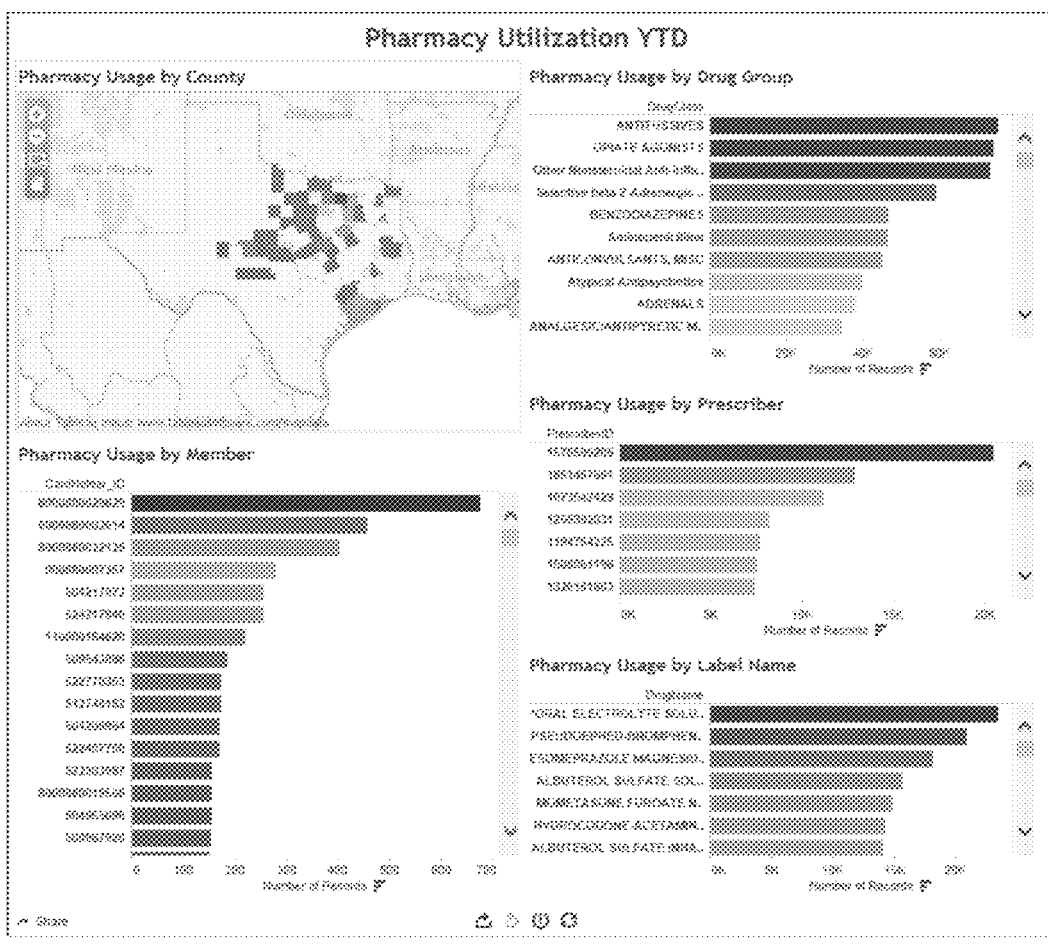
Figure 16:
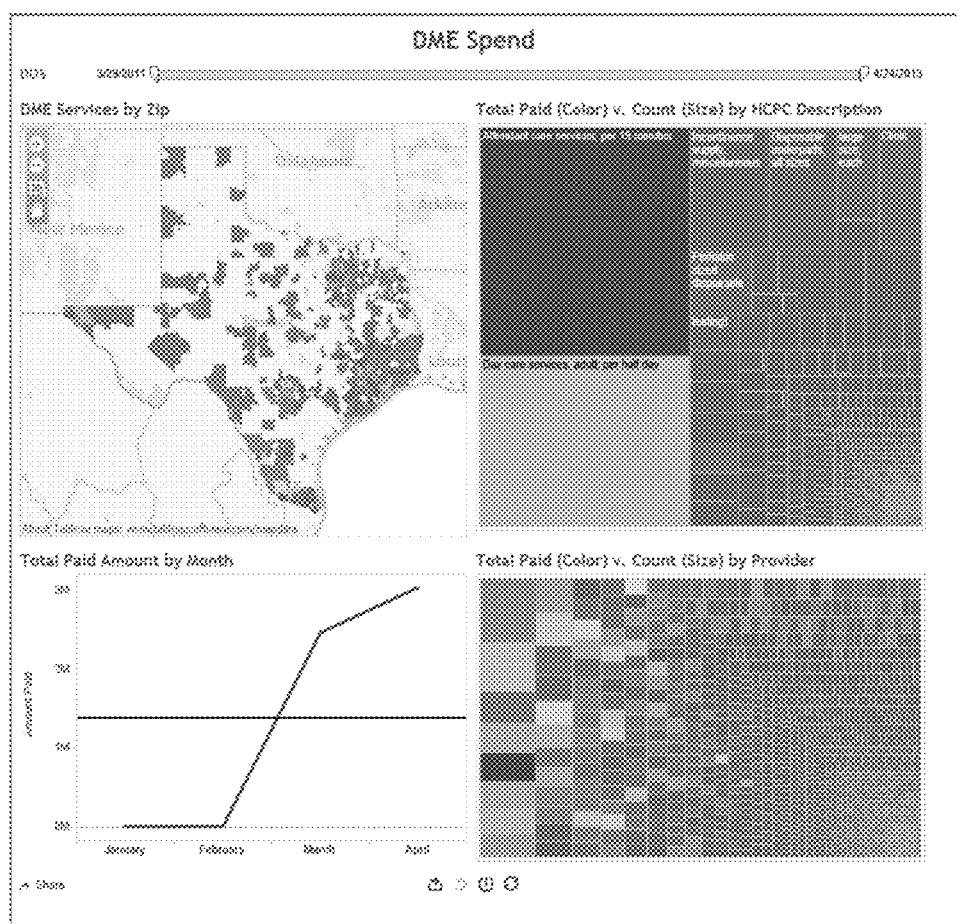
Figure 17:
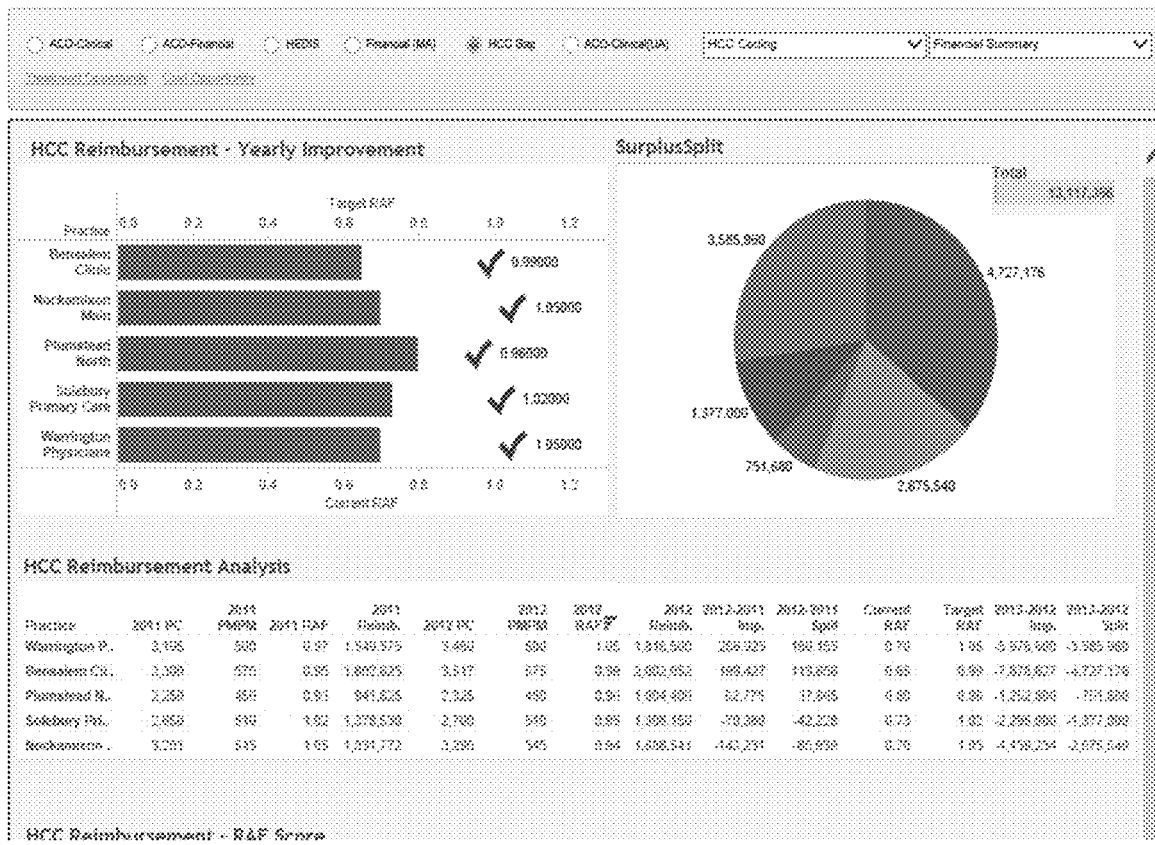
Figure 18:
Figure 19:
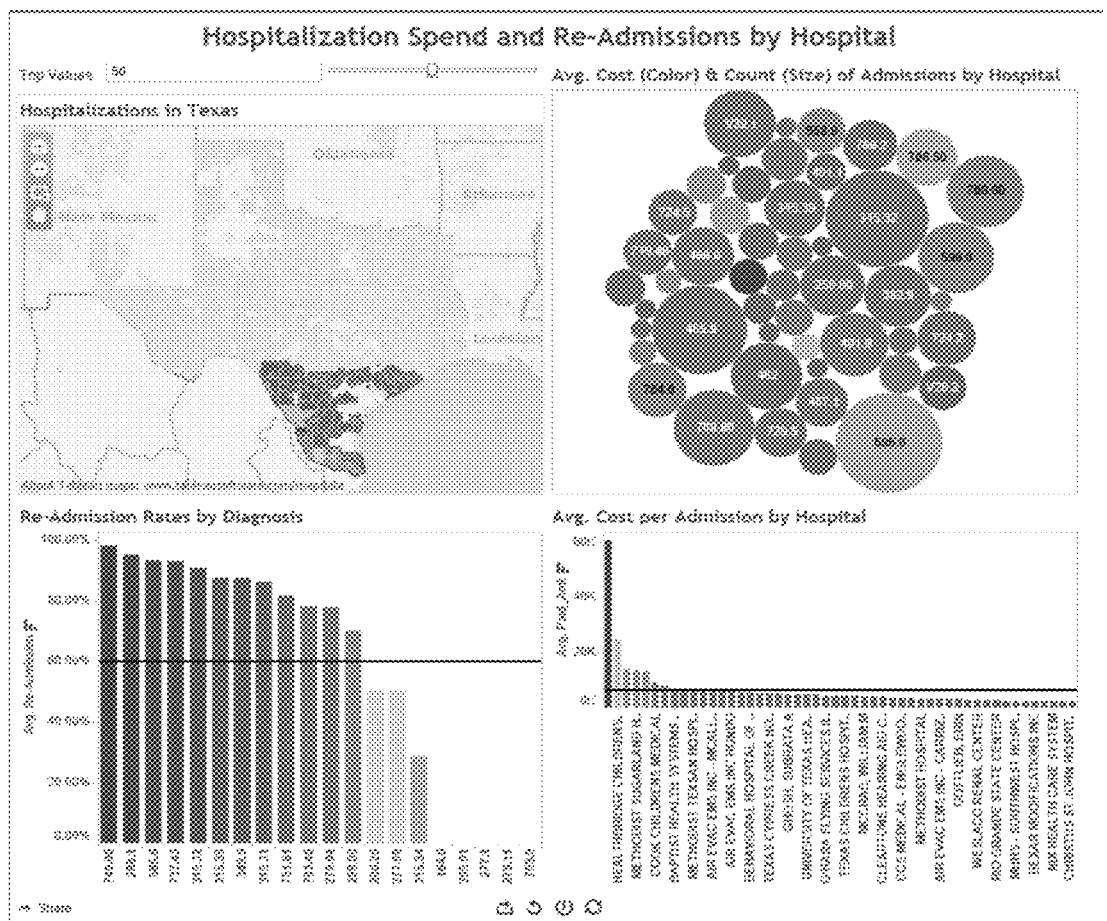
Figure 20:
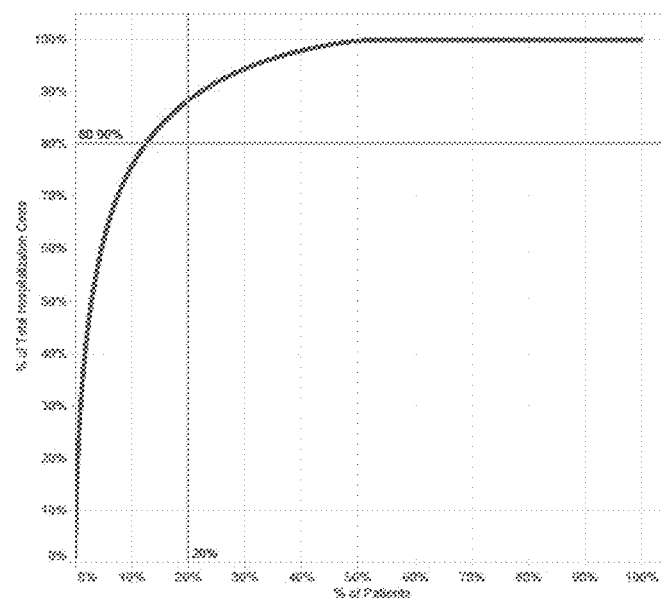
Figure 21:
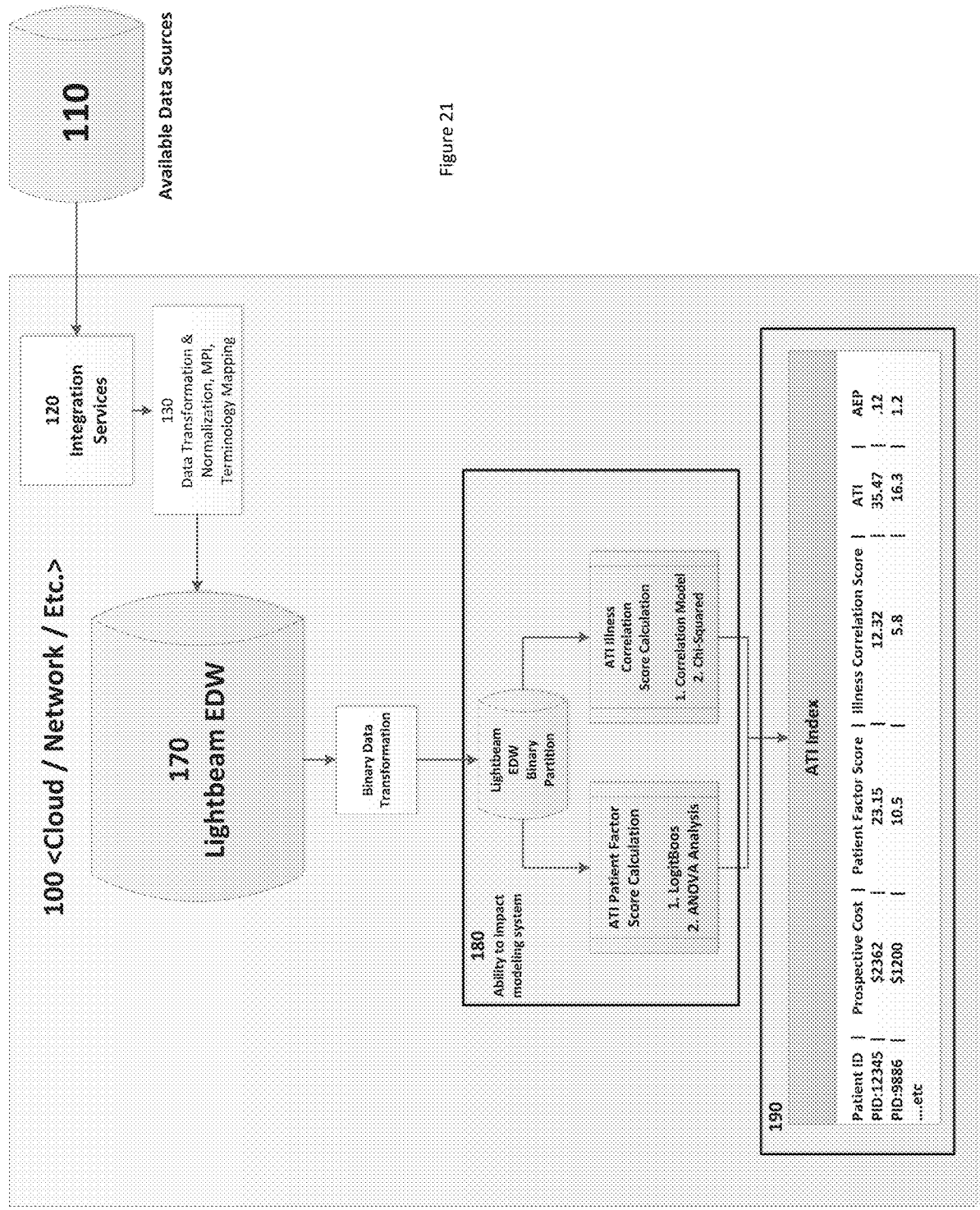
Figure 22:
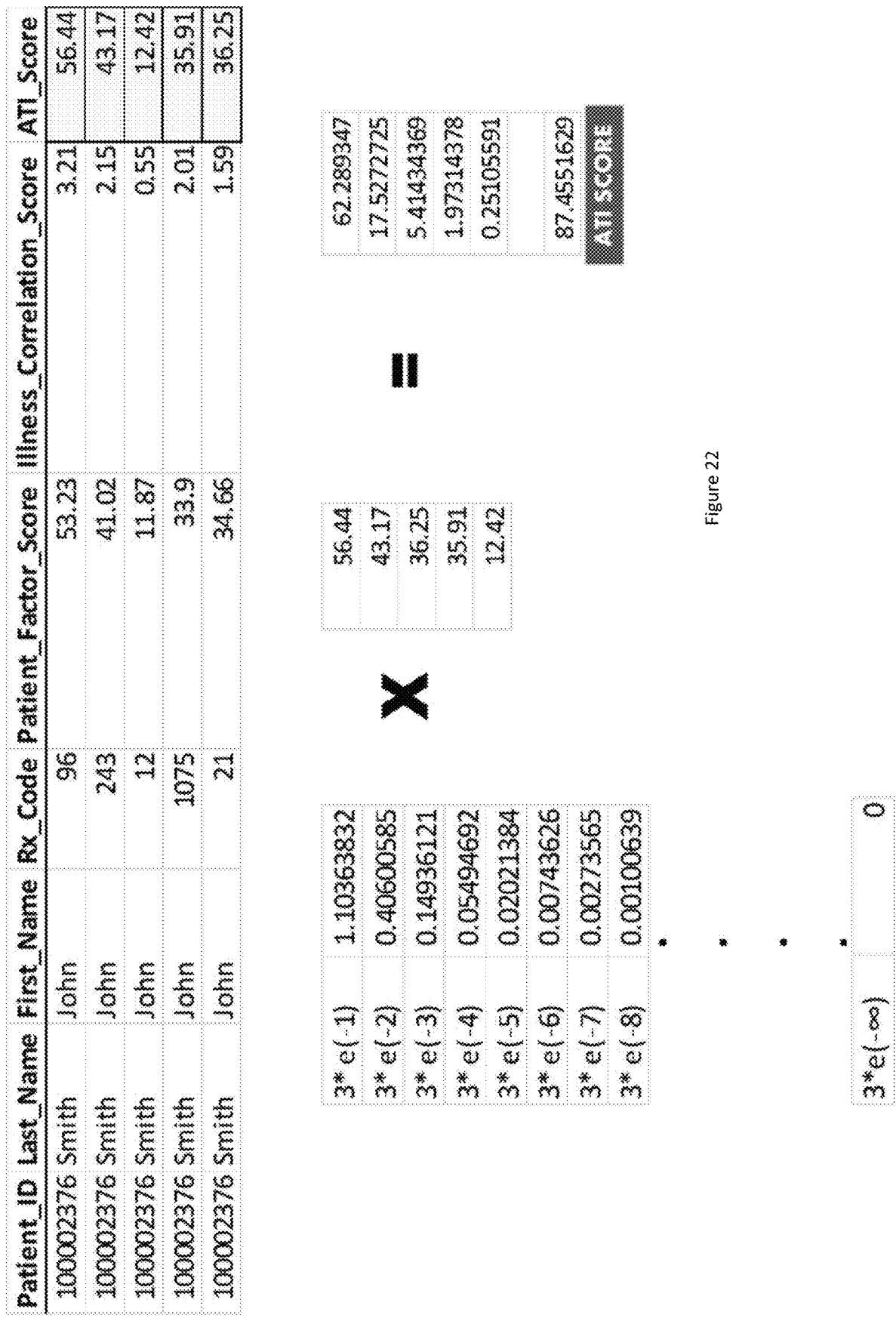
Figure 23:
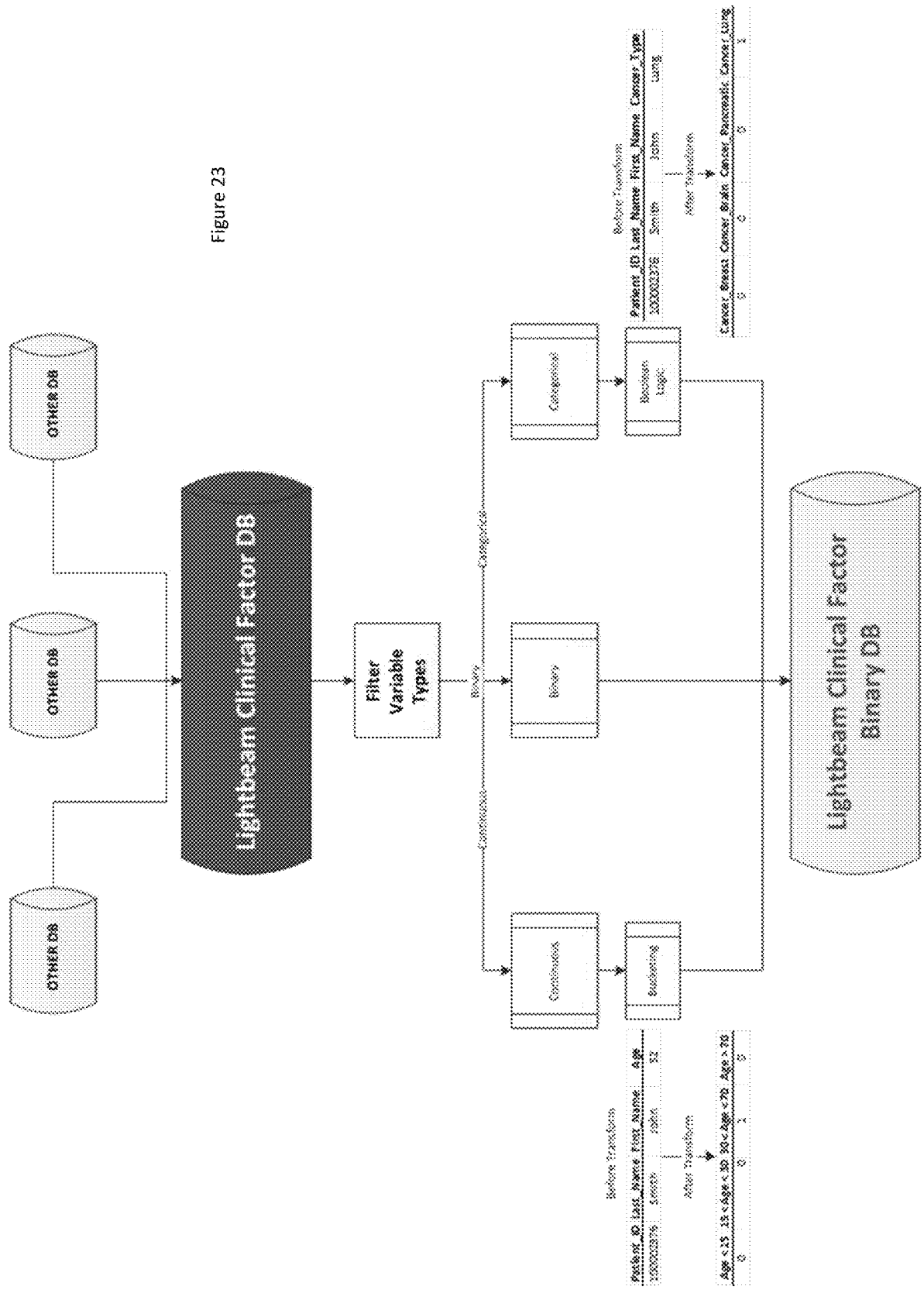
Figure 24:
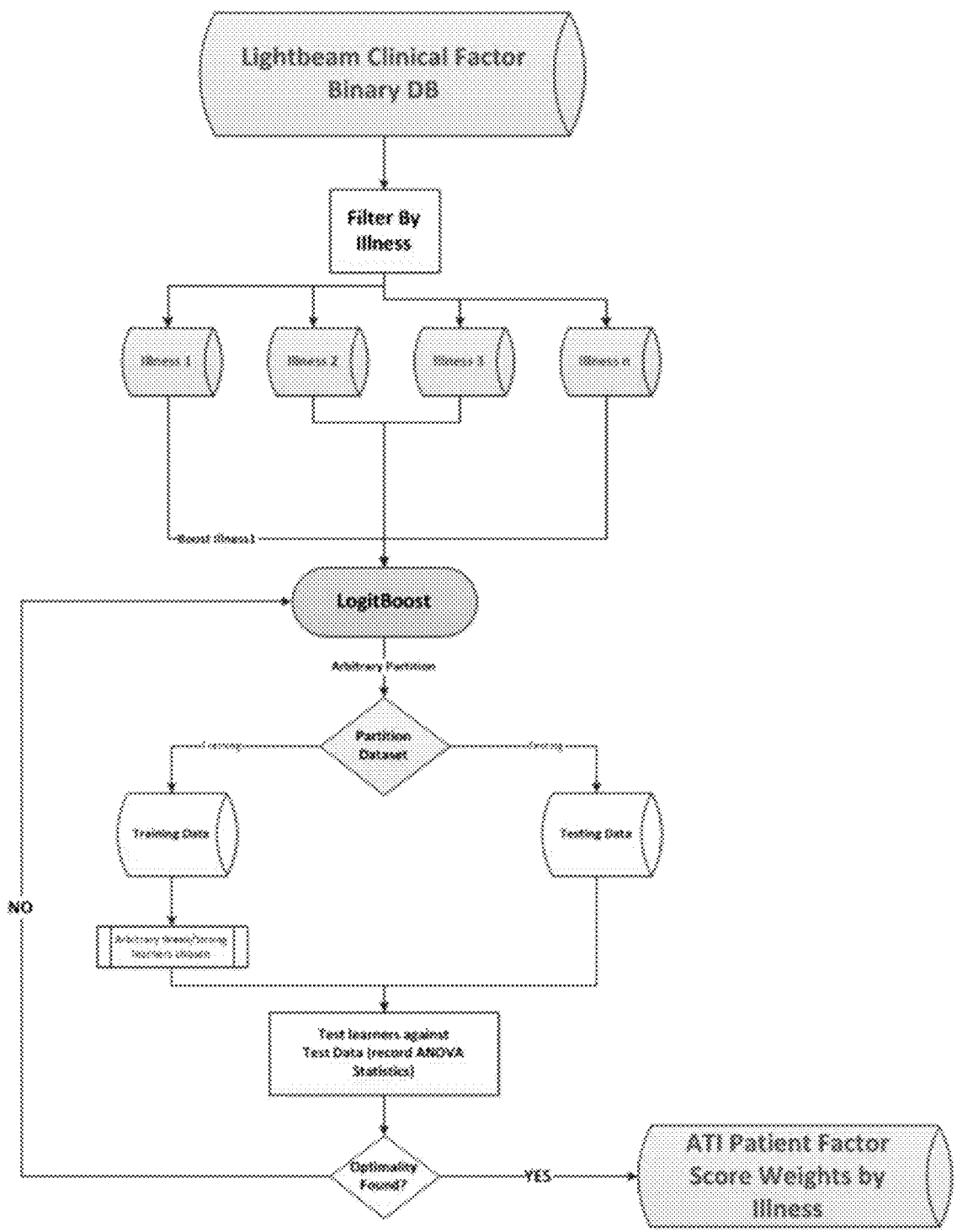
Figure 25:
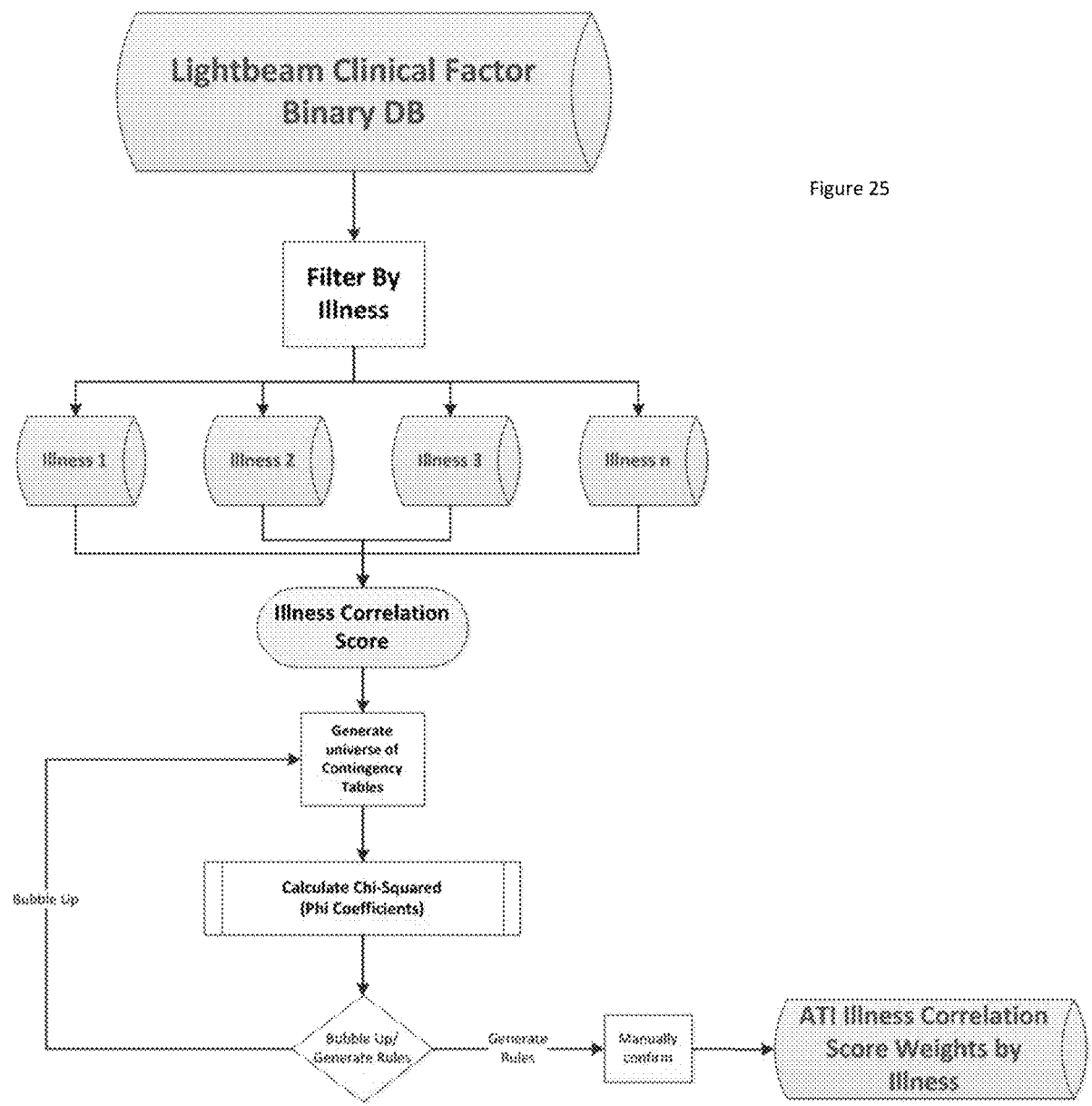
Figure 26:
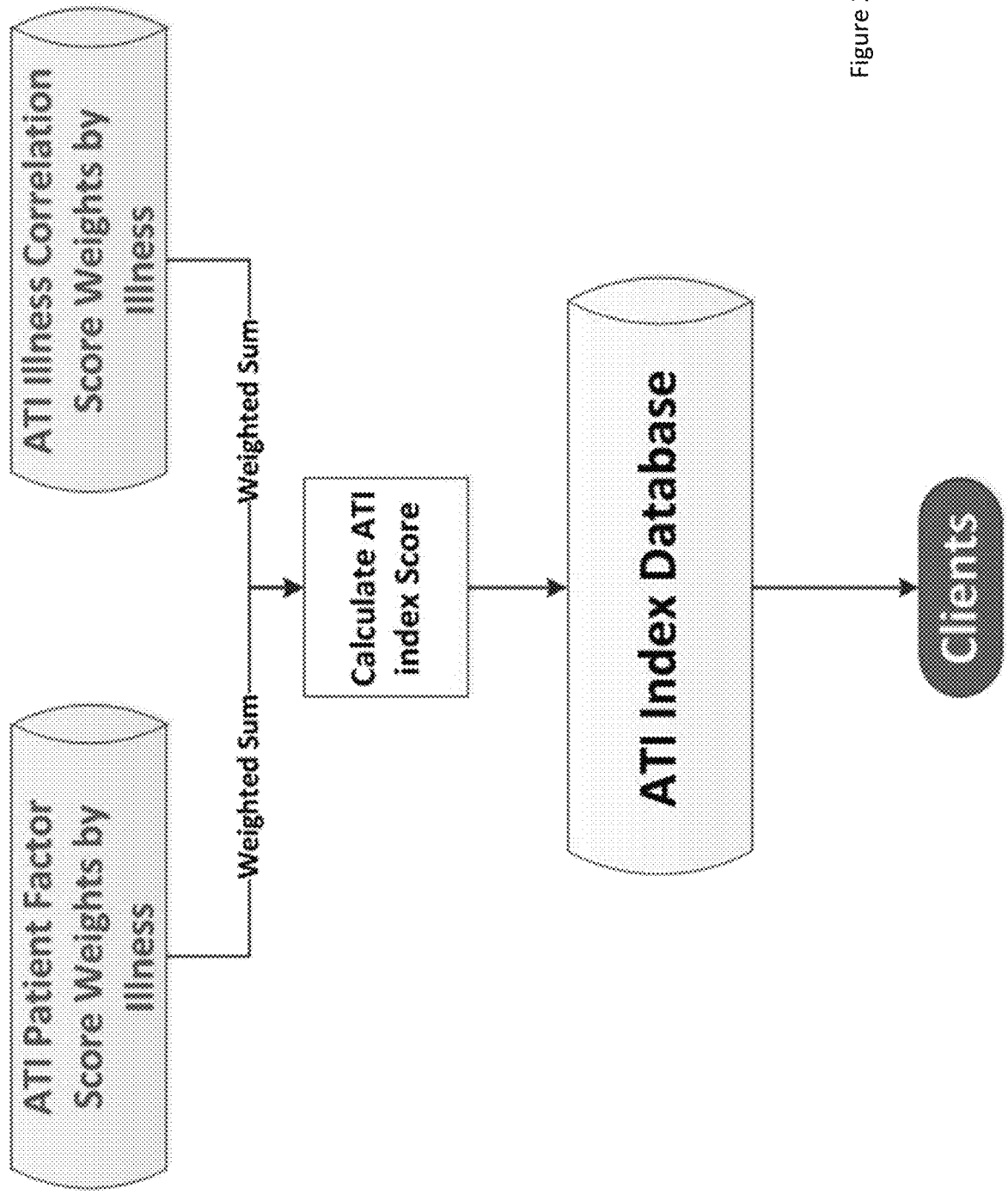

FIGS. 10-13 illustrate one of the ways the system visually and graphically depicts performance and quality scores, i.e., by depicting an example of the system's use of color shading to visually illustrate compliance and noncompliance; darker shades of red being used in FIGS. 6, 7 and 8 to draws users' attention to the providers with the lowest quality scores and an area needing improvement, and inversely, the darker the shade of green, the higher above the target value a provider, or group of providers are rated, FIGS. 6-9 also illustrating how the system allows a user to spot quality problems for a group of providers and then drill down into problem areas, to individual providers or patients;

FIGS. 14 and 15 illustrate another way that the system can graphically represent provider performance against quality measures with the use of color shading and geo mapping to indicate problem areas, and how quality data can be sorted and presented regionally, and then uses color to point a user to areas requiring attention. FIG. 14 showing how a user will see that providers in Ohio have a lower quality score and can then click there to see the providers in that area, FIG. 11 showing how a user can see which counties in Texas have the lowest quality scores, and showing how clicking on that county filters the data shown in the bar charts and then further allows a user to see what providers have the lowest quality scores;

FIG. 16 illustrates the application of heat map technology to health quality measures and provider performance data, the size of the block and color being usable to indicate volume of patients and distance from target value;

FIG. 17 illustrates the system's presentation of performance and quality data in a bar chart or pie chart;

FIG. 18 illustrates use of the system to drill into a specific measure and to then show provider scores against that measure's target values;

FIG. 19 illustrates the system's application of geo maps to illustrate compliance and/or a problem area and then its use of bubble charts, with the size of a bubble indicating the number of patients in the sampling and the color indicating status against the measure;

FIG. 20 is a pareto chart showing health quality data presented by the system; and FIGS. 21-26 are schematic block diagrams showing various aspects of the system.

DETAILED DESCRIPTION

A system is provided for monitoring the performance of a health care provider. The system tracks, analyzes, and compares the overall performance, improvements in care, cost, and quality of service of a health care provider.

For the purposes of this application a health care provider is defined as (but is not limited to) a medical provider, payer, care manager, care person, care team, nurse practitioner, physician, physician assistant, physician team or care team, or anybody involved in the delivery of care. In addition, the system can also review and collect data on groups of providers, a practice, practices, a health system, an ACO, a department within a payer or any hierarchy. The system also allows comparison of individual providers, or group of providers to other individuals, or other groups, benchmarks, comparative benchmarks and targets. Information regarding healthcare providers, can be collected through multiple sources as well as 3rd party data sources in batch and real time data exchange and also from historical data.

The system's ability to support batch and real time exchange of data from multiple sources is a significant factor in providing accurate and timely provider analytics, compliance against recommended care plans, trended quality scores, and tasks. First, the data that is collected may relate but is not limited to a provider(s) productivity, hospital systems, claims, labs and patient monitoring devices, financial records, credit scoring agencies, EHRs, HIE's, prescription data from pharmacies and PBMs, genomic databases and search engines. Next, the collected data that is provided is analyzed, transformed, and mapped in EDW to a provider, care manager, care team, insurer or provider organization. Finally, the system measures, stores, and presents a provider's performance metrics including, but not limited to ACO, HEDIS, STAR, P4P, other health quality measures, cost of care, utilization, patient's individual and aggregate risk score, error rates, patient/member satisfaction, readmittance rates and care opportunities. It also graphically and visually highlights downward and upward trends over time as well as trends further from the target or median range.

In some instances the system may also be capable of assigning a task when comparing the level of performance by cost, outcome, utilization and quality metrics of the provider's productivity. Each task that is assigned to a user may be weighed against factors that may include but are not limited to the activity that's linked to a task generated by a 3rd party tasking system, potential for cost avoidance, ability to impact the outcome, risk to patient, adverse events, and the urgent nature of the task and time to complete the task. Additionally, negative factors such as a care gap, non-compliance with a measure, over utilization, or a treatment opportunity, may be taken into consideration in determining whether or not to have a given provider continue a task, or whether or not to assign a task to a given provider. The system may also track total open tasks, total closed tasks, the time to complete each task by the user, and/or how often the user logs into the system to check for assigned tasks.

In other words, a system is provided for selecting and monitoring the performance of a health care provider through the use of real time and historical data from multiple sources. The system may include a database and a processor that may be connected to the database and to the internet, the processor being programmed to retrieve, via the internet, and store in the database, healthcare data relating to a health care provider's historical, i.e. pre-selection, performance e.g., productivity, efficiency, cost, etc., from hospital system records, claims records, lab records, data obtained from patient monitoring devices, financial records, credit scoring agency records, EHRs, HIE's, prescription data from pharmacies and PBMs, genomic databases and/or search engines. The processor may also be programmed to determine whether a provider should be selected from a group of providers to perform a task. The processor may be programmed to make this determination by obtaining from the database and assessing the provider's historical performance with regard to quality measures, cost targets, utilization and quality metrics, productivity, and/or other desired outcomes; against a pre-determined standard such as health quality measures such as ACO, P4P, or HEDIS measures, STAR ratings; or clinical guidelines, and/or 3rd party measure programs, and, optionally, taking into account a patient's individual and aggregate risk score.

The processor may also be programmed to monitor post-selection healthcare data relating to the provider's performance of the task, and to generate a graphically and visually coded reporting metric comprising displays of downwards and upwards trends in the provider's performance of the task against historical and real time data.

The determination of whether the provider should be selected to perform the task, may include selecting the provider to perform more than one task and assigning a weighting to two or more of those tasks based on each task's importance to a patient's health. The weightings may then be taken into consideration in determining whether the provider should continue one or more current tasks and/or whether the provider should be assigned one or more additional tasks.

The generation of a reporting metric may take place in the processor with the processor monitoring and reporting on the status of an assigned task, e.g., closed tasks, open tasks, system usage, and/or the total value of tasks completed. The generation of a reporting metric may include the generation of reports in the form of, for example, charts and graphs that indicate whether the provider is meeting performance standards by complying with quality measures, cost targets, utilization and quality metrics, productivity, and/or other desired outcomes.

Figure 1:
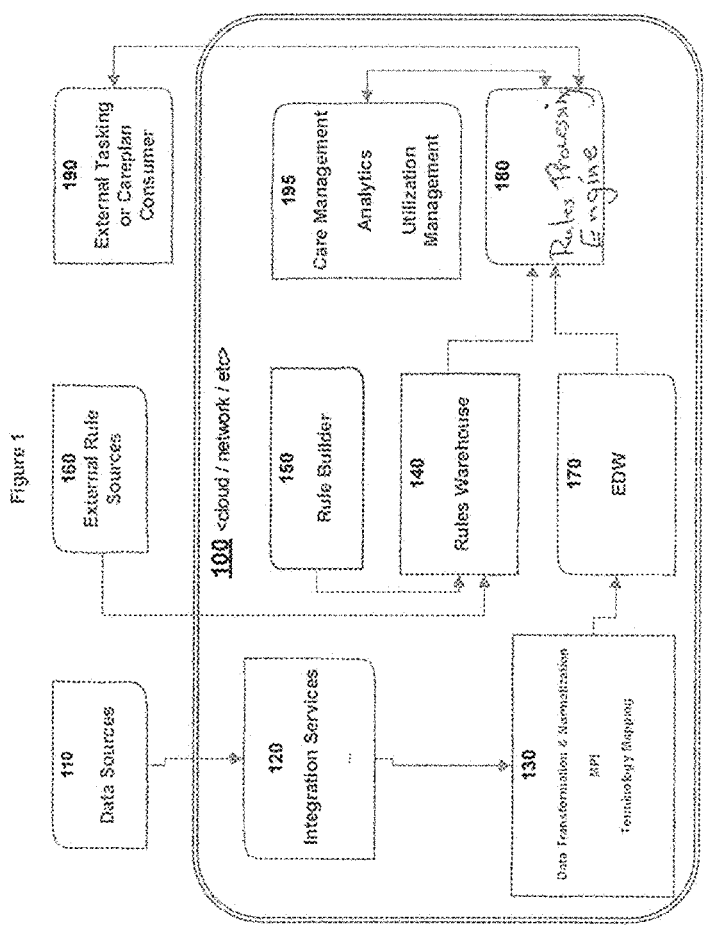
Figure 2:
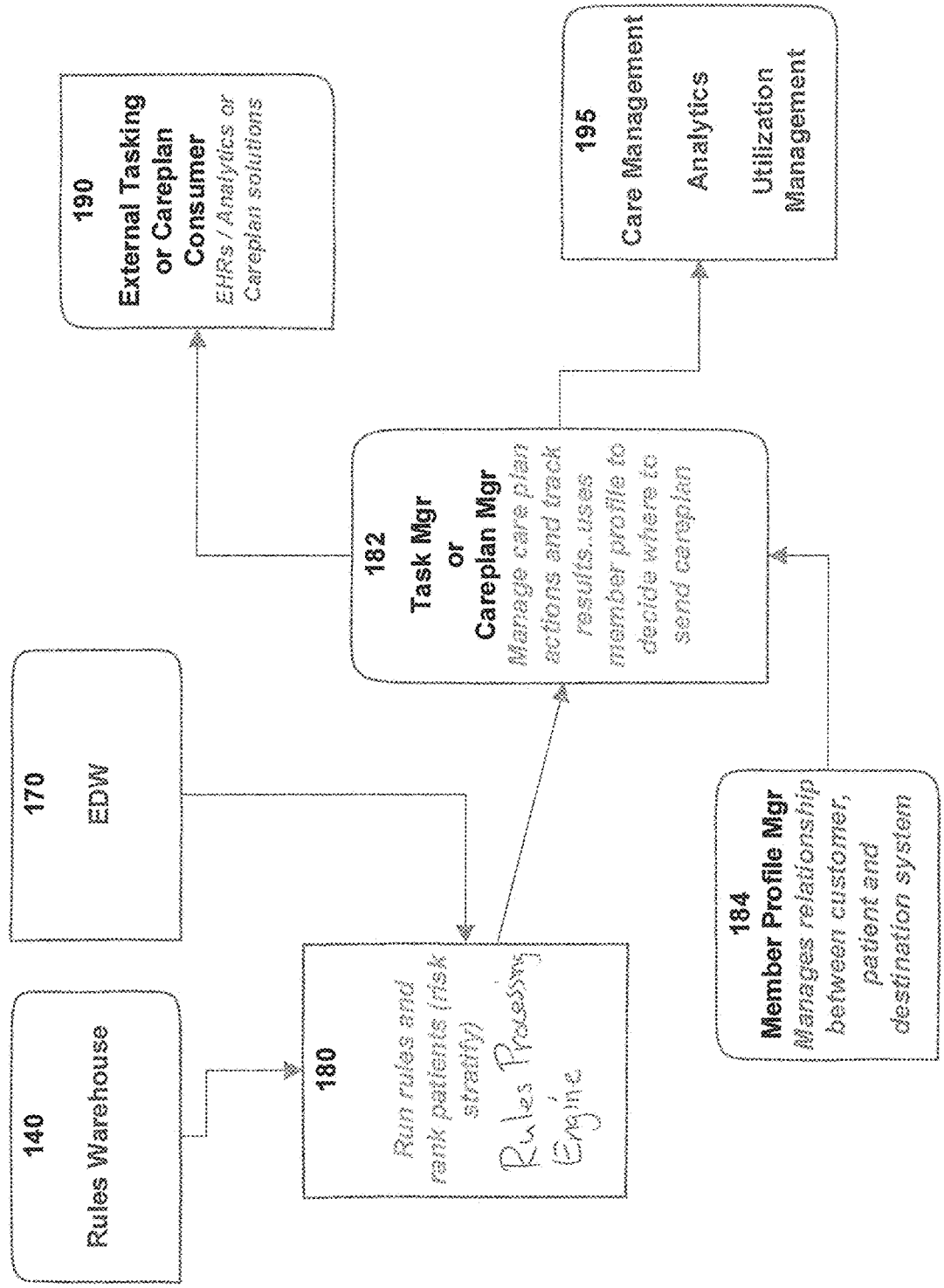
FIG. 2 is a representation of additional functionality of the rules engine, more specifically a part that manages care plans and tasking as well as an embodiment of the system that manages site profiles to facilitate communications.

Referring now to the embodiment shown in the drawings, FIG. 1 represents a healthcare data ecosystem 100 configured to gather broad and discrete data on a real time basis from multiple disparate data sources 110. All data that upon observation could be related to or a factor in deciding the appropriateness of care for that patient will be assembled into a consumable format. The Integrations Services 120, Data Transformation, Normalization, MPI, Mapping 130, Rules Building 150 and Rules Warehouse 140, Electronic Data Warehouse 170, Rules Processing Engine 180, Care Management and Utilization Management 195 and Analytics 195 are performed in by servers and made available via a cloud, web, TCP/IP, VPN and other types of connections. Data Sources 110, External Rule Sources 160 and External Tasking 190 represent third party data sources that are transformed for consumption, or third party applications that will consume this output.

Discrete data is gathered from multiple sources 110 including but not limited to ambulatory systems, inpatient systems, health information exchanges (HIEs), payers, care management systems, hospital systems, claims data, prescription data from pharmacies, pharmacy aggregators and PBMs, labs, patient biometric monitoring devices, credit score agencies, genomic databases and sources and search engines. The ability to support real time exchange of data is a significant factor in providing accurate and timely population, payer, patient and provider related analytics, notifications and tracking.

The Integration services layer 120 provides the transport infrastructure and supports current and future standards based interfaces such as HL7, CCD, CCR, XML, claims, and where applicable the Integrating the Healthcare Enterprise® (IHE) profiles used to integrate such as xdr, xds.b etc. It also supports custom interfaces, capable of reaching directly into source systems to extract data.

Data transformation and normalization 130 facilitates the mapping of data from disparate data sources using various terminology, codes and abbreviations into a normalized data set within the enterprise data warehouse (EDW) 170. The normalization will facilitate the execution of analytics on the dataset as a whole and provides a more complete and comprehensive view of patients and populations, as well as providers and payers. The data is linked by a Master Patient Index (MPI) 130, cleaned, and mapped to a healthcare data model in the data warehouse 170 to create a complete chart, referred to hereinafter as a clinical patient summary.

Site Data Links and Care Communication Link Tables will be maintained in a Site Profile Manager 184; it creates maps that link providers, patients, payers to their sources and each other, even when they were not connected by a specific transaction or data source. The system stores the source of each data stream and relevant caregivers, payers, locations of service and providers in that system to enable linking them from a communication, tasking, care plan delivery and monitoring standpoint. Some of these sources include but are not limited to inpatient systems, ambulatory systems, patient owned devices, HIEs, PBMs, Prescription Aggregators, pharmacies, labs and payer systems. A key factor in the system will be the retrieval of Communication link data related to care givers, care managers, providers, including Primary Care, Specialist, Nurse as well as Family Members hospitals, plans, or other individuals involved in the "Care Team" of a patient.

Site data links are used to provide cross reference links between external systems with related data, for example a provider in two systems could be referenced in their native systems with different identifications (IDs) yet are the same for purposes of tracking and associating data and coordinating care. The site data links provide the details on source system and will be used to facilitate communications back to the providers in their routine workflow. It will provide a number of critical services such as identifying when data is redundant, creating a complete picture of the providers involved in caring for a patient, understanding what type of information needs to be pushed back to the providers and to what providers the data should be pushed. It will include, but not be limited to linking the individual IDs for each provider and patient from each external data sources. By way of example, patient data is collected from an ambulatory EHR that indicates a provider ID and name. Data is then collected from a hospital system with a different name for the provider such as Robert vs. Bob, as well as additional data for the same patient. The provider and patient data has different ID numbers from their various external data sources but Site Data Links correctly identifies that they are the same provider and patient using a couple of data sets that typically do not change (e.g., social security number), identifies and de-dupes redundant information, normalizes the data and creates a unified normalized data set from the disparate data and/or disparate systems. It also stores a complete record of the original source data from each external data source and what source system the provider used. The Site Data Links utilizes deterministic and probabilistic models to identify when redundant information exists and when it should be consolidated into a unified clinical patient summary (a normalized data set).

Evaluation of Prebuilt Rules is performed by rules engine 180. The system will facilitate the evaluation of rules for single chronic disease states such as Diabetes, COPD, and CHF or for multiple co-morbidities as well as rules designed to highlight financial, preventive and wellness screenings or other types of gaps. These rules are typically available in text format and are not linked electronically with EDWs, EHRs and Care Management systems to be evaluated and acted on. The problem is solved by organizing them into pre-populated rules that are linked to and evaluate specific logical elements contained in the EDW 170. Rules create actions based on a user applying conditional logical expressions to data elements in the EDW. A user with the appropriate permission may be allowed to create, access, utilize or even modify pre-built rules 140. The rules are made available to end users in either a hosted or cloud environment or downloaded and imported into their environment.

The Rules Builder 150: A unique aspect of the essence of this disclosure is that it allows users to create rules 150, 160 that are designed to identify people, populations, providers, payers, care gaps, cost variances, quality variances, cost and quality trends, etc. without having to know the underlying complexity of the data schema in the EDW 170 or how to use a programming language. The rules builder 150 represents the data elements logically in terms that users of the rules builder 150 will be able to relate to, because of their background in healthcare, and abstracts the physical aspects of the database making it easy for subject matter experts (SMEs) to support rule building. Thereby reducing, or altogether eliminating, the number of people these SME's need to interact with when modifying or adding a new rule. This type of "Rule Management" should reduce the barrier to entry for clinical SME's that currently have the knowledge to construct rules but frequently are hampered by the cumbersome process to get rule sets built with the products available in the market that require programmers, data modelers, business analysts, DBA's and the SME all to be involved in the process of constructing rules today. The rules builder 150 eliminates the need to have programmers write programs to contrast the queries that would accomplish the same search as that provided by the rules builder 150.

The rules builder 150 supports a robust set of data points from the EDW 170 that represent normalized data collected from 110 by Integration Services 120 and organized into a format 130 consumable by the rules engine 180 executing the rules stores in 140. The Warehouse schema, contained in EDW 170 will be leveraged to facilitate data storage from across healthcare and non-healthcare data sources 110. Data sources will include but not be limited to Inpatient Systems, Ambulatory Systems, Medical Devices, Smart Phones, Urgent Cares, Pharmacies, labs, prescription aggregators, financial services, search engines, genomic databases and claims sources as well as additional types of information previously mentioned herein, or not reference in this document.

Rules that are pre-loaded in the rule warehouse 140 can be shared with and accessed by users through the cloud and accessed by a browser, the web, or integrated into third party applications 190. This is a particularly useful aspect of the disclosure as it allows users to avoid the cost, labor and complexity of building and maintaining rules. A new customer 110 may be allowed to connect 120 to their data into the EDW 170 and benefit from the utilization of existing rules 140. It's important to note that the rules used to manage healthcare's clinical and financial metrics are constantly changing, and therefore need to and can be modified by users. Pressure to reduce cost and improve quality is growing. These pressures are driving new reimbursement models, treatments, clinical protocols, wellness, immunization and prevention guidelines, new government initiatives, and quality measures. Quality improvement organizations as well as payers and provider wishing to improve their own cost, utilization and quality measures are increasingly searching for ways to track patient and personal compliance with actionable data in the real-time to identify care, quality and cost gaps. There are many more examples including simply wanting to identify patients and populations in need of a health risk assessment, with missing or incomplete information, a change in social status or adding fields like "lives alone" or "driving status" to a rule that's operates a diabetic measure. Therefore, rules may be loaded into the rule warehouse that are either; a) built by a user with rules builder 150, or b) assembled by External Rule Source tool 160, or c) modify and save existing rules. These rules are stored in the rules warehouse 140 and organized into a consumable format that allows them to be compared to specific logical data elements stored in EDW 170. The rules builder 150 and rules warehouse 160 are accessible via as a hosted, web or desktop application.

The rules builder 150 is used to create rules, based upon combinations of logical data elements that can include any data field contained in the EDW 170 including but not limited to types of data elements and types of data. Data that by example could include numeric values, text, clinical, financial, social, medical economic values, and data represented by and including standardized nomenclature. The rules builder 150 allows a user to create conditional expressions based on logical data elements that are stored in EDW 170. These logical data fields can be added to existing rules or onto a completely new rule using the rules builder tool 150. The user can attach a conditional expression to any data element that the system will use to identify information that needs to be reported or acted on. This conditional expression acts as a trigger. Information that could be included, but is not limited to financial or clinical gaps, financial or clinical trends, patients, populations, providers and quality gaps. By way of example, the EDW contains logical data elements that represent and store a patient's blood pressure and medications. The rules builder 150 allows a user to browse through available fields contained in the EDW. To speed selection the EDW fields will be grouped to facilitate easier selection. Once the user selects the field used to store a patient's blood pressure they then place that field into the expression used to define a new rule. The rule can also include other fields such as age, weight, body mass index, etc. The user can then attach a conditional expression to blood pressure field like "greater than" and instruct the system to create a rule that identifies all patients with a blood pressure >120/80. Additional fields can also be added and include conditional expressions so that a user can develop a specific rule that identifies patients with blood pressure over 120/80 who are also >50 years old and have not had a prescription for a class of blood pressure lowering medications within the past 6 months. Or for diabetic patients, who are over a certain age and have not had a foot or eye exam within the past 12 months or had a HA1c.

Figure 3:
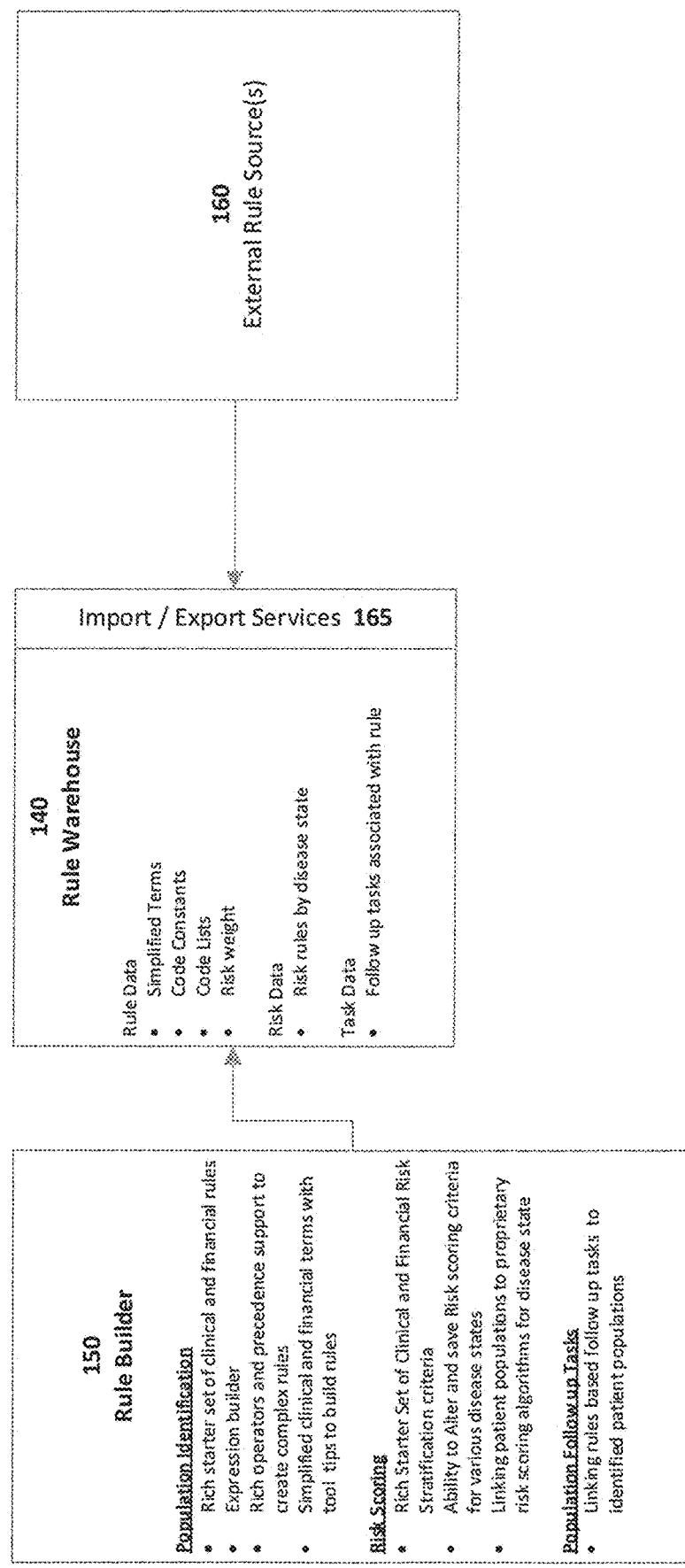
FIG. 3 illustrates additional detail relating to rule management and the rules warehouse.

External Rule Sources 160 and Rules Builder 150 allows for a user to take the guidelines provided from reference sources, and often contained is a text file, pdf, spreadsheet, HTML form and quickly create electronic rules with actionable tasks attached to each. These rules while available in text format are typically not linked electronically into the system to be evaluated and acted on as patient/provide/payer related events occur. Rule importing provides the ability to import rules from third party guidelines and content vendors as well as, but not limited to the governments website, universities, pharmacies, government agencies, quality improvement organizations, research organizations, customers and users of the product, payers, provider organization, pharmaceutical companies, compound pharmacies, care management organizations, clinical measures programs, laboratories, etc. The system allows for the transformation of guideline content from various sources to be converted into electronically executable content. The ability to bring in rules from third party sources, based on established or agreed specifications and terminologies, can be automatically loaded into rules warehouse 140 using the External Rules Sources tool 160. Where agreed upon or existing specifications, nomenclature and terminologies exist; the resulting rule will be associated with, cross references and mapped to corresponding fields and specific data contained into EDW. A standard API or standard format 165 (FIG. 3) is an import/export services layer used by the third party content providers to publish and output their updated guidelines into a format that can automatically be uploaded by external rules source 160 and stores in rule warehouse 140.

By way of examples, rules created by either the Rules Builder 150 or External Rule Sources tool 160 will be designed to evaluate and identify patients or populations for single chronic disease states, such as, but limited to Diabetes, COPD, and CHF or for multiple co-morbidities. These rules will also be able to identify patients, populations and providers and payers with overdue, pending events, incomplete data, or quality measures. Rules can also identify patients, providers and payers that have patients and populations with data that needs to be acted on such as annual HRAs, wellness and preventive screenings, identifying risk factors, identifying and reporting compliant and non-compliance with quality measures, identifying both over and under cost utilizations, comparing cost, utilization and quality measures against benchmarks and reporting aberrations or outliers. Identifying patient and providers whose actions, or lack thereof, are leading to avoidable or preventable costs. The system facilitates the creation of rules that identify patients and populations with; care or financial gaps, clinical or financial trends or variances, or in need of care or medical management. Additional examples could include managing the treatment of populations, as the output of rules will be patient populations identified as treatment opportunities based on aforementioned criteria or formatted to support measure programs. These may be standard and outlined by CMS such as PQRS, HEDIS, ACO or Stars, or custom rules built to identify patient populations in need of treatment. The output will also include all associated providers and payers as well as any associated information contained in the Member Profile Manager 184, Site Data Links 184.

The rules builder 150 and External Rule Sources 160 also allow a user to attach a ranking, assign an acuity level, or risk stratification level within each rule. The rules builder 150, 160 allows users to assign a value that depicts higher levels of acuity, ranking or risk to support the risk stratification of patient(s), populations, payers and providers identified by the rule. This allows users to sort, filter, list, view, highlight, stratify or rank patients who are in need of care and the providers or payers responsible for that care, and identifies or flags items that are of an urgent nature. Rules contained in the rule warehouse 140 and accessible to users of care management and analytics 195, or to users via integration with their third party application 190, the cloud or web-based applications include a risk stratification, ranking or acuity level. The rules builder 150 includes built in stratification criteria that are based on factors such as disease risk, potential harm to the patient, potential financial impact to providers/payers, previous cost, likelihood of readmission, risk of additional adverse events, risk to the patient, potential future cost, cost avoidance, ability to have a favorable cost of quality improvement or additional user definable criteria. Stratification, or ranking or acuity criterion that is published in the medical industry is also considered. These canned set of stratification criteria that are based on individual diseases or related to multiple co-morbidities will be available as a rule in the system. Users, with the appropriate authority and permission levels will have the ability to modify, adjust or personalize risk stratification, acuity or rank 150. This risk stratification is a crucial part of identifying the smaller subset of a very large population that may be trending towards critical health issues and allowing caregivers to focus on this subset to provide better care and reduce the financial impacts of these patients on the system. The risk stratification method matches data on patients against the rules to determine where on a relative scale a particular patient falls. If the patient has a higher risk, directing more resources to that patient may better assist that patient than one that has a lower risk. The risk stratification method may change the allocation of resources and is describing in patent application 61/993,444, filed on May 15, 2014, and is expressly incorporated herein by reference. This will also allow the system to identify patients that may not be at a high enough acuity to warrant Care Management and facilitate Patient Education and less intense care management being done by the provider's offices and care givers to ensure that they do not get to a critical stage. And for trending, aggregation and accumulation of individual ranking, risk and acuity scores for patients to then be measured, tracked and reported by individual providers, groups of providers, provider organizations, health systems, care managers, groups of care managers, payers or any subsets of plans and programs within those payers and provider organizations.

By way of example; the system will address a critical factor of risk stratifying patient(s), providers, payers and population rankings, apart from determining which patients are in need of an intervention or evaluation (Treatment Opportunities), based on factors such as, but not limited to single or multiple disease combinations, HCC Code(s), a patients social history, family history, medical history, economic data points, credit scores, search engine activity, prior charges, their velocity and frequency of care, ADL scores, information gathered from HRAs, admissions or discharges from hospitals, current medications, a change in medical status, a change in social or marital status, a change in social status, medication compliance, complexity of medication compliance, exercise and activities, risk behaviors, drug to drug interactions, addictions, alcoholic intake, family support, lives alone, individual and specific diseases, co-morbidities, depression and behavioral health disorders, age, BMI, recent admission or discharge from care, participation is a specific quality improvement initiative, genomic data or any other field in the EDW 170. Apart from the aforementioned examples, the results of this risk stratification will be prioritized lists of patients that payers, providers and health care entities can use to target the patients with the highest potential for positive results and cost avoidance. Or to target the providers or responsible parties based on the accumulative or average risk scores for the populations assigned to that provider, payer or care manager. The system allows a user to evaluate and track the total risk scores and risk trends for an individual person, population, payer, provider or providers, or any program that stands to benefits from such risk measurement.

The rules builder 150 also allows users to associate goals, or ideal outcomes within the electronic care plans with each rule. Or, said another way, each rule stored in the rules warehouse 140 contains instructions that it will use to direct the external tasking and care plan consumer 190—care management 195 the recipient as to the goal and the type of care or action 182 the person is in need of. The system will also facilitate the linking of this risk stratified patient pool individually or in mass to a closed loop care plan that is comprised of workflows, tasks and a specific care plan related to complete care of the patient by all related care team members, or activity that a provider, care manager or payer needs to perform on a group or population when a rule interrogates the patient's data and receives a positive match. Meaning, when the information contained in the patient(s) chart matches the conditional expression it launches a message to 182 and flags that patient record with the acuity/risk score and specific action needed to be taken. Those messages will be processed by the communications manager 182 or 184 and are discussed in detail as follows. Components of the care plan will include typical treatment guidelines, treatment goals and specific instructions, order sets and other types of recommended activities for patients with a need for intervention, preventive or wellness screening. It will build upon these electronic guidelines by linking the tasks to be performed by various members of the care team into groups and setting up tasks for each item and the responsible member of the care team. In addition to the Guidelines for treatment the System will support the modification of these "Care Plan Templates" by users to facilitate special conditions and goals that they may want to factor into the care of patients and populations. When a rule encounters a positive match for a patient, provider or payer it creates a transaction or message in Care Plan and Tasking Manager 182 and 201. Leveraging Site Maps 184 and Partner Care Plan Profile tool 202, meta data as well as additional data sources the system generates an outbound message 204 that writes a task in the tasking or workflow module used by the provider or care manager in their native environment 206.

Care Plan Integration with a native Partner System 206, that is also possibly also a Data Source 110, is a key attribute of this system, according to some embodiments. The system will facilitate the linkage of these care plans into the systems used to document care, often referred to as EHRs for a given provider or care manager. This integration will be directly to the system of record, stored in the Site Data Map 184 that providers, or other users, use 206 to facilitate seamless access to the data of the care plan and will leverage open APIs 207 available from most of the significant electronic medical record (EMR) vendors, examples of systems that provide rich integration capabilities are Epic, eCW, Cerner, Greenway, Allscripts and NextGen. The system 204 also facilitates; integration into the tasking and messaging capabilities of these systems 206 and linkage of a personalized care plan, 201 and 202. Using the vendors integration profile available to external entities and bases on the information stored in 184 and 202 the system knows the type of system the care plan is being delivered to and tailors the care plan components 201 and 202 to a format that's compatible with and native that system. Information such as order sets, goals, patient education materials, personal information, care plans, specific test or interventions, and other types up updated medical information will be made available to be linked and/or directly imported into the system 206 native format and workflow. The system will also facilitate the transmission of care plan related activity back to the Care System to ensure compliance or Non Compliance of the recommended Care Activity. Where API's, standards or support from vendor systems (206) does not exist the Client Agent 204 will create a task or message and imbed it directly into Partner System 206 using Partner API Tool 207. The imbedded task, message or notification will be completely compatible with and treated the same as a task, message or notification that would be created by the Native System.

Tasking and Tracking: The system 182 provides rich tasking support for any items relevant to overall "Care Workflow." Tasks and their corresponding care plans are tailored for any type of disease, preventive/wellness screening and are specific to each patient, provider and system 206. One component of this workflow will be the system-generated tasks and another component includes the corresponding care plan that the task links to. Tasks are linked to a form on server 201 that includes a care plan, treatment guidelines, stated goals, histories, risk score, other risk factors, medications, third party interventions, etc. Any information contained in EDW 170 can be drawn upon and incorporated onto that form. Each form also contains the necessary components that are specific to partner systems 206 and will be used to incorporate that information directly into those systems 206. The tasks are also weighted (acuity, risk score) to notate the impact of noncompliance or completion and specified timeframes that are relevant to the patients overall health status. By way of example, the following illustrates some types of tasks that need to occur for a patient with diabetes.

Provider Office→Schedule Office Visits that are quarterly and Yearly, including reason why—foot exam, eye exam, vascular study, etc.

Provider Office→Provide Patient Education Material related to Physical Activity and weight loss Provider Office→Issue Prescription, evaluate compliance and record Non Compliance during visits for Physical Activity, Diet, Medication Compliance Provider Office→Order Lab Tests, evaluate results and record them Provider Office→Evaluate Patient and report progress, rules are included to detect if something like blood sugar is trending poorly and the system could then generate a task in the provider office system and notify them of such.

Patient→Maintain a Level of Physical Activity

Patient→Take Medication

Patient→Provide recent blood sugar levels

Patient→Comply with recommended Diet

Patient Family→Copy any or all Provider Office or Patient messages to one or more care givers, guarantors or family members.

Tasks, including the aforementioned acuity levels, reason, patient, care plan, follow-up date will also be reported to Care Management module 195. All of the information contained in the EDW 170 for that patient will be accessible to users of 195 and linked directly to the patient and the task. Completion of these tasks and attainment of goals will be tracked 195 for compliance and reporting purposes 195. The analytics capabilities 195 can also format this information for consumption by External Systems 190. The frequency of reminders, the recipient and the priority of tasks will be linked to the acuity or risk level of a given task as well as the number of attempts made without a response. By way of example, if a medication-to-medication interaction indicates a high risk of serious injury, the system will indicate a higher acuity/risk and then escalates the urgency further by copying care managers, supervisors, the patient, additional providers, other user, family members (using the information contained in the member profile manager 184) if there is no initial response. It can also track and trend non compliance for non-urgent matters such as; lack of diet control for obese and pre-diabetic patients that could lead to a diabetics health state and a deteriorating/costly condition. The analytics platform 195 tracks compliance and longer term trends to show providers and payers that specific factor(s) indicates patient or population are trending towards the next level of the disease, so that the appropriate intervention can then be identified by a rule stored in the rules warehouse 140 and performed by the analytics system 180. Another significant component of the system will be "Alerts" and "Tasks" that relate to a change in patient status such as moving from one stage of a disease to another as a result of non-compliance or other factors such as readings from home monitors or biometric devices.

The systems analytics platform 195 tracks and associates the impact of task compliance and non-compliance to the patients and populations overall health status and risk score. The analytics model 195 is also tracks and trend risk scores, quality scores, quality metrics, goals achieved by patient, population, payers, care managers, care coordinators, providers or groups of providers. Over time these tasks will be tracked 195 to develop a profile of compliance and risk scores for patients, population's, members of a care team, and relevant persons or entities notified of "performance" as it pertains to a pool of patients in a providers case, or the patient themselves. Risk scores are also tracked and trended over time and reportable by the aforementioned categories.

The performance reporting 195 tied to the provider, payer, patient or population for risk, compliance and better health status also is used to track rewards, compliance and bonuses for individuals, care managers, patients, payers and providers. Rewards and penalties currently include, but are not limited to, government rating systems such as STAR ratings, HEDIS, ACO Measures, shared saving pools, gain share arrangements and other forms of quality or cost based bonus metrics. The care management analytics module 195 also allows for the grouping of information so that a supervisor can track, trend, report and compare metrics like risk scores and tasks completed for their patients and populations thereby allowing the supervisor to truly measure the effectiveness of the interventions and of care managers, providers, quality improvement initiatives, etc. Today, there is not an effective way to track and compare their initiatives, workloads, cost savings, quality improvements and staff efficiency against one another. For patients and populations the rewards include better health as well as, for example, inclusion in a commercial program that awards points to the patient each time they submit their required information either by texting, the web, a biometric device, IVR or speaking directly to the care manager. Information could include blood pressure, blood sugar, and peak flow rate, and pulse oxygen, validation that they took their medications or exercised.

Care Plans 201 can be disease based, preventive in nature or linked to an entire population and tasked to external source systems 206 when actions need to take plan. For example, the system identifies multiple patient overdue for a procedure, lab, medication refill or wellness/preventive screening and generates a list with each person identifies in that list. As shown in 182, the System supports a standard set of Care Plans that outline the Plan Details as shown in 201. These plan details include details such as, but not limited to, the name of the care plan, the goal, associated disease state, the original source, and the criteria for the patient to be eligible for the Care Plan. By way of example, the criteria that determine a patient's eligibility in a care plan could be associated with them being in the top 3 percent of the risk stratified patient pool associated with one or more patient identification rules 140 that are part of the base rule/measure set.

The care plan will also include the general "Plan Workflow" as show in Item 201*b* (not to be confused with a simple task list). This Plan 201 and workflow will encompass the following;

Standard Guideline Tasks: related to Standard Treatment Guidelines as shown in 201*b*.1. An example of a task related to a basic diabetic care guideline might be the scheduling of a quarterly office visit.

Customized Guideline Tasks: The plan supports Customer modified guideline tasks as shown in item 201*b*.2

Non Guideline Tasks: The system also supports tasks that may be part of a workflow but not necessarily associated with the "Clinical Guideline" shown in FIG. 201*b*.3 but necessary for the workflow overall such as the authorization for Referrals, Tests, etc.

Each of these disease, action specific or care plan tasks, or goals, will be associated with a specific role in the patients care team using Site Profile Manager 184 including, but not limited to, the Provider, Primary Care Provider, Cardiologist, Podiatrist, Internist, Ophthalmologist, Urologist, Pulmonologist, Admitting Provider, Discharge Provider, Surgeon, Oncologist, Endocrinologist, Nurse, Patient, Patient Care Taker, Care Manager, Care Coordinator, Social Worker, Transition of Care Team, Home Health Worker, Family Members. As mentioned above, each associates task and care plan sent to each role includes a standard time for the completion of the task or follow-up on the task. Site Profile Manager 184 also stores each care team members preferred method of communication. If a care team member utilizes a Partner System 206, the Client Agent 204 will transmit the task to that system along with the necessary components to imbed that task and care plan into that system. If the patient, family member or person is not using a Partner System, the system will store a profile 184 and 202 listing their communication preference. Preferences could include Portal 205, their External System 190, 195, texting, smart phones, IVR, browser, phone, onsite visit by social/care worker, etc.

Prebuilt Care Plans are stored in the system 182, 201 as default care plans and associated with specific rules, goals, financial or clinical guidelines or disease states such as Diabetes, COPD, and CHF etc. Any of these prebuilt or default can plans can be modified by users with the appropriate permission using Care Plan manager 182.

Partner Care Plan Profile

Figure 4:
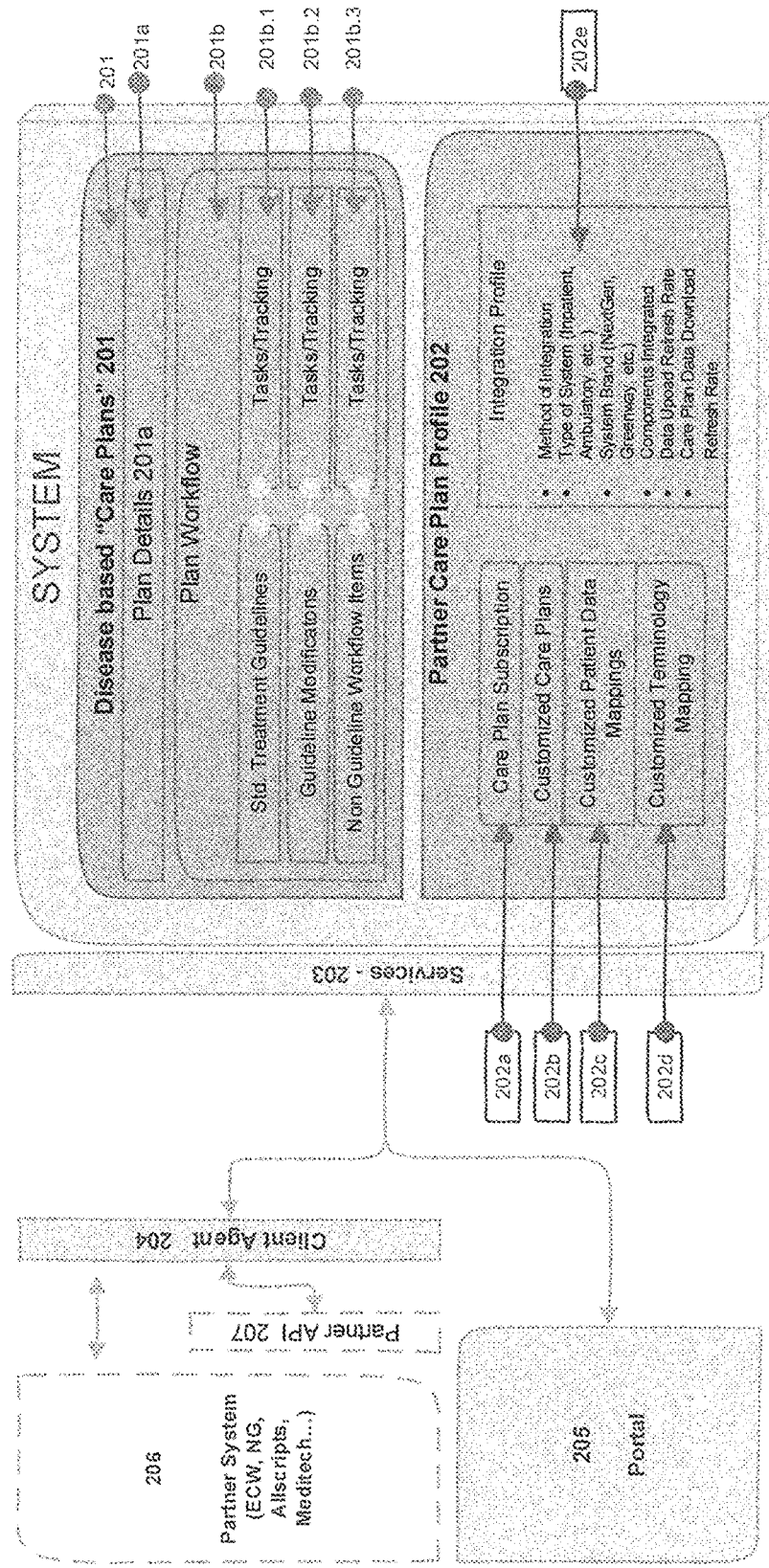
FIG. 4 is a workflow diagram showing care plans and tasks being created and transmitted to provider systems and illustrates how rules are connected to tasks and how tasks are connected to care plans and how tasks and care plans are connected to external systems, portals or partner systems.

Partner Registration Portal 205 allows an integrating system, wishing to connect to register through Portal 205 (FIG. 4). During registration basic information will be collected as describes in 202*e* to facilitate the Client systems registration. Once known, Partner Systems 206 with previously identified methods of integration and established tasking/messaging/communication routines will connect through Client Agent 204. Most of the leading Inpatient and Outpatient EHRs and Care Management System are Known Partner Systems and communications are already established.

Information obtained from Portal 205 may be used to determine which API to assign to that new system. Partner Care Plan Profiles may be built and maintained, as further described below;

Partner Care Plan Profile 202 maintains a communication profile, or API, for each Partner System 206. Once registered by Portal 205, or recognized as an existing Known Partner 206, partners will be able to link their system to the system via the Client Agent identified in item 204.

Integration Profile (Item 202*e*): The integration profile for a given client entails the unique aspects of the Partner System 206 and the method of integration. Some of these items will be discovered by the system install process for the system client agent (204), and some will be input into the system by Portal 205, where the element cannot be automatically detected. The items that will be stored by the system will facilitate seamless integration with the Partner System 206 and customize content and optimize the data being delivered to the system based on each profile, these items will include:

Method of Integration 202*e* which outlines the use of Browser based components for integration or rich API based integration. This also specifies what interfaces (standards based or custom) are used to integrate such as HL7, CCD, CCR and where applicable the IHE profiles used to integrate such as xdr, xds.b etc Each profile will some of the following information used to integrate tasking, and care plans directly into the providers native EHR and workflow.

Type of System: (202*e*) Inpatient, Ambulatory, Care Management, etc.

System Brand: (202*e*) NextGen, Greenway, Allscripts Epic, Meditech, Siemens, etc.

Components (202*e*) integrated such as Tasking, Integrated Care Summary (CCD), Discrete Care Plan or Document based Care Plan Data Upload Refresh Rate: (202*e*) The rate (Real-time, Hourly, . . . ) at which data is uploaded to the System for analysis Care Plan Data Download Refresh rate (202e) (Real-time, Hourly . . . )

Domain Data Synchronization Rate (202e): The rate at which domain data such as Provider Lists, Users, etc are synchronized with the system.

Care Plan Subscription (202a): Partners can also outline which Care Plans they want to subscribe to from a set of Care Plans stored in 182. This information will be stored so the system knows which Care Plans to auto update if changes occur to the base care plans in the system.

Customized Care Plans (202b): Partners can also copy Care Plans and customize them to their own needs and modify certain components of the Care Plan that are not mandatory for that Care Plan Customized Patient Data Mappings (202c): Allows customers/users to review the standard Data Mappings available for various types of data such as demographic data, Clinical Summary Data and the typical system locations, for that data, and modify them to reflect where this data may come from in their system.

Customized Terminology Mappings (202c): Customers/users can review what terminology sets are available and supported within the system and map user defined items to standard items in the system. This can be applicable and particularly useful to mapping items such as medications or other user defined clinical items that normally map to a code system such as NDC, ICD9, ICD10, LOINC, but in some cases do not.

Operational Workflow: This section outlines the operational flow of Care plans for specific patient's profiles 184 and related tracking of tasks between the system and the Partner System 206.

In a typical workflow when a patient is enrolled in or assigned to a care plan by a user or a rule, and the patient is scheduled for a visit, the Partner System will send an outbound request to the system via the Client Agent (204). This request will retrieve the Care plan that is recommended for this patient based on the rule and complete patient clinical history available at the Server 170. The system will then create a Task Notification 183 for the Relevant Care Team Member or Care Team Group (that was synchronized with the system at install time), in the partner system 206. The system will also link into the Partner system 206 and populate other items such as the care plan itself using the Integration profile information for the particular client. This could include the Care Plan itself in the form of recommendations for Care, Goals, Patient Risk Profile, Patient Education Links, Order sets for different tests to be performed as part of the guidelines. Also depending on the integration profile (202e) and the partner vendor system 206 for that client there may be the ability to send back task completion information from the partner as tasks are completed in the partners system via the Client Agent (204) and sent back to the system in the cloud to reevaluate the Patients Risk score and the progress of the patient through the Care Plan.

The system will also send alerts for tasks that are not completed to the partner system based on the due dates and reminder intervals that exist for the various tasks as the patient progresses through the Care plan.

In another typical workflow, the patient in need of care may be identified, by way of a rule 150, and assigned to that care plan associated with that rule to that patient. Then, the task according to the Integration Profile 202e may be created and transmitted 204, and that task, message or communication may be imbedded into Partner System 206. The user assigned to the care team opens that task in their native workflow as they would any task created by the native system. The task is linked back to the care plan (202a and 202b) and stored in the task manager 182 via the cloud. The care team member reviews the care plan and accepts them into their system using the Customized Patient Data and Terminology Mapping tools (202c and 202d). Utilizing this workflow, a care team member sees a task or message in their normal workflow, opens it and then, with a single click, accepts the care plan into their native systems workflow.

Similarly, if the Patient is linked to the system via a Member Portal 190, the patient will also receive texts, reminders, instructions, referrals, and patient education directly through the Member Portal. Responses from that patient will also be logged against the patient's information and used to reevaluate the patients overall risk score, next steps and actions to be taken.

Actions associated with the Task and information related to the care plan that is received by client agent 204 from partner system 206 will also be logged and trended 185 over time to develop compliance profile for the care team member. As well as for patients and populations they care for to allow for supervisors to be aware of a given Care Team member's performance.

Similarly a patients compliance with medication regimen, Review of Patient Education Material, Reporting of Device Data and Social and clinical values over time will be used to augment or adjust the risk profile and trends for this patient.

By illustration of an example, an aspect of the system will include the ability to react to data collected 110 from cellular and Bluetooth® home monitors such as pulse oximeters, spirometers, glucose meters and digital scales. A rule, or guideline, can be built 150 to trigger an action for a patient whose clinical information is trending poorly but has not yet contacted a provider or visited with the ER. Using the inventive system, these patients can be identified, their physicians notified as described above to make sure they receive the proper care. Inversely, the same diabetic patient might have gone days/weeks with high blood/sugar levels causing damage to their vascular, renal, extremities and eyes without them knowing. In a sense the system is predicting a future adverse event and acting on the information improve the patient's health and reduce healthcare costs for ER and hospital visits. Adding to the complexity, to properly identify and care for a person with diabetic nephropathy requires validating that the patient's receiving treatment from multiple disparate medical entities. This information may be collected and assembled from insurance companies, laboratories, other EHRs, hospital systems, the patient, pharmacies and the EHR. Once assembled it may be compared to the proper care guideline to insure the patient's compliance with the overall care plan for that disease. The patient has not had a foot within the requisite time period the Care Manager identifies the gap and creates a task in the NextGen EHR. If that provider doesn't act on this information the care manager may be notified and can escalate or forward to a different provider. After something like a blood sugar spike is detected multiple parties need to be notified with multiple actions to be taken, and tracked to insure the patient is back on the right path.

Figure 5:
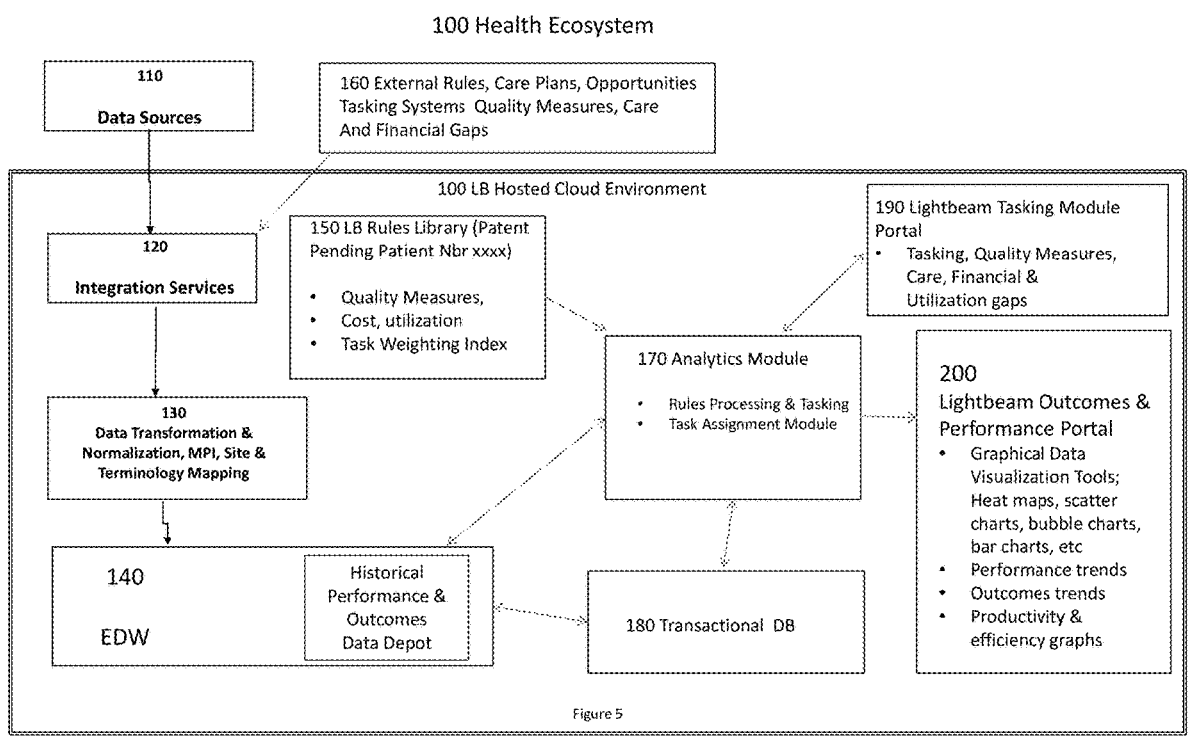
FIG. 5 shows a healthcare data ecosystem with an embodiment of the system, and illustrates the capture of data used in measuring providers' performance against health and quality measures through to the graphical presentation of those measures.

FIG. 5 shows components and relationships to 3rd party applications and users. Provider and payer performance data may be collected, analyzed, and graphically presented. Performance may be measured and graphically presented against health measures, other providers, quality, cost, utilization, workload and efficiency.

The system measures, tracks, trends, and graphically represents care, quality, and financial metrics for providers, provider care teams and care managers. It allows provider organizations, insurers and risk-bearing organizations to compare performance against measures such as, but not limited to, ACO and HEDIS Measures, STAR Ratings, as well as clinical guidelines. The method compares, tracks and presents productivity by user, groups of users, provider(s), practice(s), insurers, care managers, care teams, care team supervisor, etc.

The method also measures, tracks, and graphically presents employee productivity. It does this by assigning a task to each user. Each task may also be assigned a weight. A task could include but not be limited to a care gap, non-compliance with a measure, over utilization, or a treatment opportunity. The system then tracks total tasks assigned and completed for each user. It also tracks the total weight for the tasks assigned to and completed by each user. The system tracks total open tasks, total closed tasks, and how often a user logs in to check for assigned tasks. The time to complete each task may also be tracked and totaled for each user.

This system provides real-time analysis of current and historical performance data by provider. The system presents on-the-fly reporting with graphical color coding, benchmarks, and drill-down capabilities.

The system may include an outcomes and performance monitor that tracks the usage of the system, assigned, closed tasks and the total value of tasks completed. Ultimately, this system measures provider and payer impact on cost, patient health scores, quality, and the ROI of a quality improvement initiative. It will track and display how much a provider, provider organization or payer "moved the needle."

The Analytics Module 170 determines and measures performance by evaluating data from multiple sources (110 & 160), collected by 120, organized by 130 and stored in EDW 140. Results are displayed in an intuitive graphical representation 200. The system measures, stores and presents a provider's performance for metrics including, but not limited to, ACO, HEDIS, STAR, P4P, other health quality measures, cost of care, utilization, error rates, patient/member satisfaction, readmittance rates and care opportunities. Data Sources 110 include, but are not limited to, EHRs, HIE's, payers, hospital systems, claims, prescription data from pharmacies and PBMs, labs and patient biometric monitoring devices, financial records, credit scoring agencies, genomic databases and search engines. The data may then be analyzed, transformed 130 and mapped in EDW 140 to a provider, care manager, care team, insurer or provider organization. To calculate and determine performance, the analytics module 170 compares data from EDW 140 to the clinical rules, measures and guidelines stored in 150. The system also pulls care and measure gaps and treatment opportunities that have been Tasked to and/or created by and stored in 3rd party systems 160. When the system is being used in conjunction with 3rd party applications 160 that create, capture, store or use Tasks or treatment opportunities quality gaps, care opportunities or quality measures, the system will combine that with data from 140 to compile a complete picture of a provider's performance. The system will also monitor, track and combine the provider's responses to each 3rd party Task. External Rules Engines 160 could include tasks that are stored in Electronic Medical Records Systems, Care Management Systems. Results are graphically displayed by the Outcomes and Performance Monitor.

For the purposes of this application, a "provider" is defined as including, but is not limited to, a medical provider, payer, care manager, care person, care team, nurse practitioner, physician, physician assistant, physician team or care team, or anybody involved in the delivery of care. In addition to individual provider performance the system can present performance for groups of the above mentioned providers, a practice, practices, a health system, an ACO, a department within a payer or any hierarchy. The Transaction DB 180 allows users to easily map performance data to a data hierarchy for grouping reports. By way of example, a reporting hierarchy might be patient, provider, location, department, practice or Tax ID, ACO, hospital, health system, enterprise, and parent organization. Within each hierarchy performance data can be grouped or reported individually. The system also compares an individual provider, or groups of providers to other individuals or other groups, benchmarks, normative benchmarks, comparative benchmarks means and targets.

The representative healthcare data ecosystem 100 of FIG. 5 may be configured to gather broad and discrete data on a real time basis from multiple disparate data sources 110 and 160. All data that upon observation could be related to provider, provider team, care manager and care team productivity will be assembled into a consumable format for analysis by the disclosed analytics platform. The Integrations Services 120, Data Transformation, Normalization, MPI, Mapping 130, Electronic Data Warehouse 170, Tasking Weighting System 150 are performed by the system on our servers and made available via our portal, the cloud, web, TCP/IP, VPN and other types of connections. Data Sources 110 represent 3rd party data sources that are transformed into the system for consumption, or 3rd party applications 160 that will also consume the output of this system.

Discrete data may be gathered from multiple sources 110 including but not limited to ambulatory systems, inpatient systems, electronic medical records, HIEs, payers, care management systems, Lightbeam's Analytics Platform, 3rd party analytics systems, hospital systems, claims data, prescription data from pharmacies, Rx aggregators and PBMs, labs, patient biometric monitoring devices, genomic databases and search engines. The system's ability to support both batch and real time exchange of data 120 may be a significant factor in providing accurate and timely provider analytics, compliance against recommended care plans, trended quality scores 140 and tracking.

The Integration services layer 120 provides the transport infrastructure and supports current and future standards based interfaces such as HL7, CCD, CCR, XML, claims, and where applicable the IHE profiles used to integrate such as xdr, xds.b etc. It also supports custom interfaces, capable of reaching directly into source systems to extract data.

A key characteristic of this system is that it maps 130 tasks, historical tasks, care plans, gaps in care, patient notifications, claims, quality, utilization and cost data with detailed, discrete clinical data from sources 160 to a provider or care manager for tracking and reporting purposes. Therefore, we are able to measure performance, outcomes, quality and utilization for tasks, care gaps and quality measures generated outside of this system. Data transformation and normalization 130 facilitates the mapping of data from disparate data sources using various terminology, codes and abbreviations into a normalized data set within the enterprise data warehouse (EDW) 170. The normalization will facilitate the execution of analytics on the dataset as a whole and provides a more complete and comprehensive view of providers, payers, and care teams as well as their patients and populations. The data may be linked to a provider or care manager 130, cleaned, normalized, mapped to a healthcare data model in the data warehouse 140.

The LB Rules Library 150 stores clinical rules, health quality measures and clinical guidelines that are created by the system or 3rd party measure programs or government agencies or quality reporting organizations. By way of an example, quality measure ACO Measure 22 includes the programmatical specifications that will be used to identify the percentage of a providers diabetic patients whose Hemoglobin A1c is <8. To determine a provider's performance against ACO Measure 22, the system determines the total number of diabetes patients assigned to the provider (the denominator) and then calculates % compliance, or score, by seeing how many have a H1Ac <8 (the numerator). The patients with H1Ac >8 are considered care gaps, gaps in care or treatment opportunities. The Analytics Module 170 may be used to evaluate individual patient/member data stored in EDW 140 on a provider basic against clinical guidelines and quality measures and then report the results to Outcomes & Performance Module 200 or 3rd party applications 190. This information may be cross referenced by provider and then compared against the rules library 150 to determine or measures a provider's compliance for quality measures, care gaps, specific predefined interventions and various quality measure programs.

The LB Rules Library 150 also stores benchmarks and targets that will be used to measure performance against a provider's utilization and cost data. A particularly unique aspect of the system lies in its ability to track provider follow-up to a notification that a treatment opportunity or care gap exists for a patent. When the Analytics Module 170 identifies a care gap or treatment opportunity it attaches it to a Task that's linked directly to the provider and presented via Tasking Portal 190. Said another way, a Task will be created when the Analytics Module 170 identifies a gap in care or non-compliance with a quality measure. Each Task may be attached to the quality measure or care gap or care plan and assigned to the Provider or Care manager responsible for the patient, and to complete the Task. By further way of example, if a patient is found to have a H1Ac of >8 the Analytics Module 170 creates a Task for a Provider and presents that Task in 190. The system also tracks and graphically represents the time between the Task creation and completion. It tracks creates performance relative to Task creation, completion, open tasks and closed tasks.

Task status can also be read from or written directly into an EHR Tasking system's 160 Workflow Module or on the web-based application 190 and access via secure cloud-based technology. The tasks can include specific instructions from the rules library 150 for satisfying and completing the task. The system's Analytics Modules 170 tracks how often a user or provider logs in and checks for tasks, their response to each task, and how long it takes to complete each task and the total weighted value of the tasks completed. The results are presented graphically on Outcomes and Performance Monitor 200.

The Outcomes and Performance Monitor 200 not only tracks provider performance against quality measures but also tracks the usage of the system, assigned tasks, closed tasks and the total value of tasks completed. The system provides for on-the-fly reporting, drill down capabilities and provides various graphical and visual representations including but not limited to heat charts, scatter charts, bubble chart, bar charts, line charts, pie charts, and/or area charts. A user can view any of these charts and drill down from an enterprise, organizational, payer, group view to an individual provider and even a patient to see the details. Many other systems generate periodic reports but don't offer this feature whenever a provider, provider organization or payer wants to review the data graphically from highest-lowest, lowest-highest compliance, payer, health system, practice, ACO or individual provider.

Charts and graphs use colors and visual tools to depict compliance, quality, above or below averages and the degree or range from the target. For example, the color green can be used to depict that a provider is compliant with a quality measure. The darker the shading on the green the further above the benchmark or target range that provider's performance falls. Red might be used to indicate that the system measures the provider's performance to be below the target value. The darker the shade of red the further below the benchmark or target range the provider's performance falls.

The system trends all data measured including a provider's health quality measures scores, tasks completes, efficiency, utiltization and cost as well as other factors mentioned in this patent. Once calculated by the Analytics Module 170 the results are stored in EDW 140 Historical Trending Depot. This enables the system to trend provider(s) performance data over time. It also graphically and visually highlights downward and upward trends. Color coding and shading may be used to denote trends that are furthest from the targeted or median range.

The Analytics Module also includes a Task Weighting System (TWS) 170 that utilizes proprietary algorithms to calculate a weighting, or specific value, for each task. The task weighting system utilizes factors including, but not limited to, the acuity that's linked to a task generated by a 3rd party tasking system, potential for cost avoidance, ability to impact the outcome, risk to patient, adverse events, urgent nature of the task and time to complete. The TWS System stores Task Weights in the Task Weighting Index 150 for future reference. The system's proprietary algorithms frequently recalibrate the individual task values. A provider's individual Task Scores are added together to create a value that represents the provider's total Task Workload, or the weighted score of the tasks that are assigned, open and completed. Task Scores for individual providers are added together to calculate create a total Task Workload Rating for groups of providers, practices, and health systems, insurers and care teams. The results are presented and trended graphically by the Outcomes & Performance Module 200. By way of example, an organization with 600 providers or care managers views and ranks employee productivity and efficiency by Task Workload completed and now has a way to identify high performers as well as under-performers. Otherwise it can be very challenging to determine if an employee (provider or care manager) can handle more work, or is completing the work assigned to them, as there's no way to benchmark employee productivity in terms of total work completed.

This description, rather than describing limitations of an invention, only illustrates (an) embodiment(s) of the invention recited in the claims. The language of this description is therefore exclusively descriptive and is non-limiting.

Obviously, it's possible to modify this invention from what the description teaches. Within the scope of the claims, one may practice the invention other than as described above.

The invention claimed is:

1. A system for selecting a health care provider from a group of health care providers, and then monitoring and reporting the selected provider's performance, wherein the system is electronically accessible by a member portal over the internet; the system including:

an electronic database;
a processor connected to the electronic database and to the internet,
wherein the system is configured to allow registration of one or more external systems for integration with the system, wherein, as a result of an electronic registration process of at least one external system of the one or more external systems, the system provides at least one application programming interface (API) that is used to link the system to the at least one external system, wherein an external system profile for the at least one external system is maintained by the system and used for communications and/or interoperability between the system and the at least one external system, and wherein the external system profile is configured in part based on the electronic registration process; and
wherein the system is configured to communicate with the at least one external system through use of the API and based on the external system profile; and
wherein the processor is programmed to:
  retrieve discrete data from one or more internet-accessible discrete data sources via an electronic data connection that uses transmission control protocol (TCP) and store at least a portion of the discrete data in the electronic database as historical performance data for each provider in a group of health care providers, and as healthcare data relating to each health care provider's historical performance, wherein the discrete data includes clinical data relating to the health of patients in a population of patients, wherein the discrete data is from at least three of the following systems or components: an ambulatory system, an inpatient system, a health insurance exchange, payers, a care management system, a hospital system, a claims data system, a pharmacy, a pharmacy aggregator, a pharmacy benefit manager, a lab, patient biometric monitoring devices, a credit score agency, a genomic database, and a search engine, and wherein at least one of the one or more internet-accessible discrete data sources is a part of the at least one external system and is accessed by the system through use of the external system profile for the at least one external system;
  normalize and transform the discrete data into a normalized data set by mapping the discrete data to a healthcare data model using various terminology, codes, and abbreviations;
  assess the providers' historical performances against each other based on the historical performance data of the normalized data set;
  select a provider among the group of providers based on the assessment of the providers' historical performances against each other, to perform a plurality of tasks;
  monitor post-selection healthcare data relating to the selected provider's performance of the plurality of tasks; and
  generate a reporting metric to be displayed on the member portal, wherein the reporting metric comprises a graphical display of an overall task workload score for the selected provider and overall task workload scores for a plurality of other providers of the group of providers,
  wherein the overall task workload score for the selected provider is based on a plurality of task workload ratings, wherein a single one of the plurality of task workload ratings corresponds to a single one of the plurality of tasks, and wherein each of the plurality of task workload ratings is calculated based on:
    the post-selection healthcare data relating to the corresponding task, wherein the post-selection healthcare data relating to the corresponding task is determined based on compliance of performance of the corresponding task with target values of a measure that is set by a third party for the corresponding task; and
    a weighting for the corresponding task, wherein the weighting for the corresponding task is based on an importance of the corresponding task to the health of a patient and an acuity of the corresponding task.

2. The system of claim 1 in which the processor is further programmed to determine whether the provider should continue a current task, based on the post-selection healthcare data relating to the provider's performance of the plurality of tasks.

3. The system of claim 1 in which the processor, in selecting a provider, is further programmed to: determine whether the provider should continue a current task based on the weighting for each of the plurality of tasks.

4. The system of claim 1 in which the processor is further programmed to determine whether the provider should be assigned another task, based on the post-selection healthcare data relating to the provider's performance of the plurality of tasks.

5. The system of claim 1 in which the processor, in selecting a provider, is further programmed to:
  determine whether the provider should be assigned one or more additional tasks based on the weighting for each of the plurality of tasks.

6. The system of claim 1 in which the processor, in generating a reporting metric, is further programmed to monitor and report on the status of an assigned task.

7. The system of claim 1 in which the processor, in generating a reporting metric, is further programmed to generate reports that indicate whether the provider is meeting performance standards.

8. The system of claim 1, wherein at least part of the discrete data originated from an electronic home monitor.

9. A system for selecting a health care provider from a group of health care providers, and then monitoring and reporting the selected provider's performance, wherein the system is electronically accessible by a member portal over the internet; the system including:
  an electronic database; and
  a processor connected to the electronic database and to the internet, wherein the system is configured to allow an electronic registration process of one or more external systems for integration with the system, wherein, as a result of registration of at least one external system of the one or more external systems, the system specifies at least one application programming interface (API) that is used to link the system to the at least one external system, and wherein an external system profile for the at least one external system is maintained by the system and used for communications and/or interoperability between the system and the at least one external system, and wherein the external system profile is configured in part based on the electronic registration process;
  wherein the system is configured to communicate with the at least one external system through use of the API and based on the external system profile; and wherein the processor is programmed to:
retrieve discrete data from two or more internet-accessible discrete data sources via an electronic data connection that uses transmission control protocol (TCP) and store at least a portion of the discrete data in the electronic database as historical performance data for each provider in a group of healthcare providers and as healthcare data relating to each health care provider's historical performance, wherein the discrete data includes clinical data relating to the health of patients in a population of patients, wherein the discrete data is from at least three of the following systems or components: an ambulatory system, an inpatient system, a health insurance exchange, payers, a care management system, a hospital system, a claims data system, a pharmacy, a pharmacy aggregator, a pharmacy benefit manager, a lab, patient biometric monitoring devices, a credit score agency, a genomic database, and a search engine, and wherein at least one of the two or more internet-accessible discrete data sources is a part of the at least one external system and is accessed by the system through use of the external system profile for the at least one external system;
normalize and transform the discrete data into a normalized data set by mapping the discrete data to a healthcare data model using various terminology, codes, and abbreviations;
determine which provider should be selected to perform a task, by assessing the providers' historical performances against each other based on the historical performance data of the normalized data set;
select a provider from the group of providers, to perform a plurality of tasks;
monitor post-selection healthcare data relating to the selected provider's performance of the plurality of tasks; and
generate a reporting metric to be displayed on the member portal, wherein the reporting metric comprises a display of an overall task workload score for the provider and overall task workload scores for a plurality of other providers of the group of providers,
wherein the overall task workload score for the provider is based on a plurality of task workload ratings, wherein a single one of the plurality of task workload ratings corresponds to a single one of the plurality of tasks, wherein each of the plurality of task workload ratings is calculated based on:
the post-selection healthcare data relating to the corresponding task, wherein the post-selection healthcare data relating to the corresponding task is determined based on compliance of performance of the corresponding task with target values of a measure that is set by a third party for the corresponding task, wherein each of the measures is selected from one or more of the following: an accountable care organization (ACO), a healthcare effectiveness data and information set (HEDIS), a situation task/target action result (STAR), and a pay for performance (P4P) payment model; and
a weighting for the corresponding task, wherein the weighting for the corresponding task is based on an importance of the corresponding task to the health of a patient and an acuity of the corresponding task.

10. The system of claim 9, wherein at least part of the discrete data originated from an electronic home monitor.

* * * * *